(12) United States Patent
Molloy et al.

(10) Patent No.: US 11,136,575 B2
(45) Date of Patent: Oct. 5, 2021

(54) TCR LIBRARIES

(71) Applicant: IMMUNOCORE LIMITED, Abingdon (GB)

(72) Inventors: Peter Eamon Molloy, Abingdon (GB); Arsen Valeryevich Volkov, Abingdon (GB); Dhaval Jaykant Sangani, Abingdon (GB); Graham Anthony Hood, Abingdon (GB); Chandramouli Reddy Chillakuri, Abingdon (GB)

(73) Assignee: Immunocore Limited, Abingdon (GB)

( * ) Notice: Subject to any disclaimer, the term of this patent is extended or adjusted under 35 U.S.C. 154(b) by 0 days.

(21) Appl. No.: 15/759,772

(22) PCT Filed: Sep. 15, 2016

(86) PCT No.: PCT/EP2016/071761
§ 371 (c)(1),
(2) Date: Mar. 13, 2018

(87) PCT Pub. No.: WO2017/046201
PCT Pub. Date: Mar. 23, 2017

(65) Prior Publication Data
US 2019/0048333 A1    Feb. 14, 2019

(30) Foreign Application Priority Data

Sep. 15, 2015   (GB) ..................... 1516277

(51) Int. Cl.
*C40B 40/10*       (2006.01)
*C12N 15/10*       (2006.01)
(Continued)

(52) U.S. Cl.
CPC ...... *C12N 15/1072* (2013.01); *C07K 14/7051* (2013.01); *C07K 14/70539* (2013.01);
(Continued)

(58) Field of Classification Search
None
See application file for complete search history.

(56) References Cited

U.S. PATENT DOCUMENTS

| 6,753,136 B2 | 6/2004 | Löhning |
| 7,312,074 B1 | 12/2007 | McGregor |

(Continued)

FOREIGN PATENT DOCUMENTS

| CA | 2906218 A1 | 9/2014 |
| JP | 2006-525790 A | 11/2006 |

(Continued)

OTHER PUBLICATIONS

British Search Report, Intellectual Property Office Patent Application No. GB1404536.3, dated Dec. 18, 2014, 3 pages.

(Continued)

*Primary Examiner* — Christian C Boesen
(74) *Attorney, Agent, or Firm* — Fenwick & West LLP

(57) ABSTRACT

The present invention relates to a library of particles, the library displaying a plurality of different T cell receptors (TCRs), wherein the plurality of TCRs consists essentially of TCRs comprising an alpha chain comprising an alpha chain variable domain and a beta chain comprising a beta chain variable domain and the library comprises more than one TRAV gene product and/or more than one TRBV gene product, wherein the beta chain variable domain does not comprise one or more of a TRBV5-1, 5-3, 5-4, 5-5, 5-6, 5-7 or 5-8 gene product and wherein the plurality of TCRs do not consist essentially of TCRs comprising a TRAV12-2 gene product from a natural repertoire and a TRBV6 gene product from a natural repertoire and TCRs comprising a TRAV21 gene product from a natural repertoire and a TRBV6 gene product from a natural repertoire.

19 Claims, 15 Drawing Sheets

Specification includes a Sequence Listing.

Schematic of cloning step used in library construction

(51) Int. Cl.

| | | |
|---|---|---|
| C07K 14/725 | (2006.01) | |
| C07K 14/74 | (2006.01) | |
| C12N 15/66 | (2006.01) | |
| C12N 15/85 | (2006.01) | |
| C40B 40/02 | (2006.01) | |

(52) U.S. Cl.
CPC ..... *C12N 15/1062* (2013.01); *C12N 15/1086* (2013.01); *C12N 15/66* (2013.01); *C12N 15/85* (2013.01); *C07K 2317/56* (2013.01); *C07K 2317/565* (2013.01); *C12N 2015/8518* (2013.01); *C12N 2015/8527* (2013.01); *C40B 40/02* (2013.01); *C40B 40/10* (2013.01)

(56) References Cited

U.S. PATENT DOCUMENTS

| | | | |
|---|---|---|---|
| 7,329,731 | B2 | 2/2008 | Jakobsen et al. |
| 7,569,664 | B2 | 8/2009 | Jakobsen et al. |
| 7,608,410 | B2 | 10/2009 | Dunn et al. |
| 7,666,604 | B2 | 2/2010 | Jakobsen et al. |
| 7,763,718 | B2 | 7/2010 | Jakobsen et al. |
| 7,785,859 | B2 | 8/2010 | Löhning |
| 8,283,446 | B2 | 10/2012 | Jakobsen et al. |
| 8,361,794 | B2 | 1/2013 | Jakobsen |
| 8,378,074 | B2 | 2/2013 | Jakobsen et al. |
| 8,519,100 | B2 | 8/2013 | Jakobsen et al. |
| 8,735,146 | B2 | 5/2014 | McGregor |
| 8,741,814 | B2 | 6/2014 | Jakobsen et al. |
| 9,068,178 | B2 | 6/2015 | Jakobsen et al. |
| 9,115,372 | B2 | 8/2015 | Jakobsen |
| 9,255,135 | B2 | 2/2016 | Jakobsen et al. |
| 9,279,122 | B2 | 3/2016 | Jakobsen et al. |
| 9,447,410 | B2 | 9/2016 | Jakobsen et al. |
| 2002/0034733 | A1 | 3/2002 | Löhning |
| 2002/0058253 | A1 | 5/2002 | Kranz et al. |
| 2002/0119149 | A1 | 8/2002 | Jakobsen et al. |
| 2002/0142389 | A1 | 10/2002 | Jakobsen et al. |
| 2005/0009025 | A1 | 1/2005 | Jakobsen et al. |
| 2005/0058984 | A1 | 3/2005 | Löhning |
| 2006/0093613 | A1 | 5/2006 | Jakobsen et al. |
| 2006/0155115 | A1 | 7/2006 | Jakobsen et al. |
| 2006/0166875 | A1 | 7/2006 | Jakobsen et al. |
| 2008/0125369 | A1 | 5/2008 | Jakobsen et al. |
| 2008/0220981 | A1 | 9/2008 | McGregor |
| 2009/0054257 | A1 | 2/2009 | Dunn et al. |
| 2009/0054258 | A1 | 2/2009 | Dunn et al. |
| 2009/0214551 | A1 | 8/2009 | Jakobsen et al. |
| 2010/0047220 | A1 | 2/2010 | Jakobsen |
| 2010/0113300 | A1 | 5/2010 | Jakobsen et al. |
| 2010/0297093 | A1 | 11/2010 | Robbins et al. |
| 2012/0027739 | A1 | 2/2012 | Jakobsen et al. |
| 2012/0190828 | A1 | 7/2012 | Jakobsen et al. |
| 2012/0225481 | A1* | 9/2012 | Jakobsen ........... C07K 14/7051 435/369 |
| 2013/0149289 | A1 | 6/2013 | Jakobsen et al. |
| 2013/0189309 | A1 | 7/2013 | Jakobsen |
| 2013/0295063 | A1 | 11/2013 | Jakobsen et al. |
| 2014/0349855 | A1 | 11/2014 | Jakobsen et al. |
| 2014/0371085 | A1 | 12/2014 | Jakobsen et al. |
| 2015/0197771 | A1 | 7/2015 | Bethune et al. |
| 2017/0051036 | A1 | 2/2017 | Jakobsen et al. |
| 2018/0340167 | A1 | 11/2018 | Jakobsen et al. |
| 2018/0340168 | A1 | 11/2018 | Jakobsen et al. |
| 2018/0346903 | A1 | 12/2018 | Jakobsen et al. |
| 2018/0346904 | A1 | 12/2018 | Jakobsen et al. |
| 2019/0048058 | A1 | 2/2019 | Jakobsen et al. |
| 2019/0048059 | A1 | 2/2019 | Jakobsen et al. |
| 2019/0048333 | A1 | 2/2019 | Molloy et al. |
| 2019/0153062 | A1 | 5/2019 | Vuidepot et al. |

FOREIGN PATENT DOCUMENTS

| | | |
|---|---|---|
| JP | 2008-504043 A | 2/2008 |
| WO | WO 99/11785 A1 | 3/1999 |
| WO | WO 99/60120 A2 | 11/1999 |
| WO | WO 01/05950 A2 | 1/2001 |
| WO | WO 01/48145 A2 | 7/2001 |
| WO | WO 03/020763 A3 | 5/2003 |
| WO | WO 2004/033685 A1 | 4/2004 |
| WO | WO 2004/044004 A2 | 5/2004 |
| WO | WO 2005/114215 A2 | 12/2005 |
| WO | WO 2005/116074 A2 | 12/2005 |
| WO | WO 2005/116646 A1 | 12/2005 |
| WO | WO 2006/000830 A2 | 1/2006 |
| WO | WO 2006/103429 A2 | 10/2006 |
| WO | WO 2006/125962 A2 | 11/2006 |
| WO | WO 2006/129085 A2 | 12/2006 |
| WO | WO 2009/059804 A2 | 5/2009 |
| WO | WO 2010/133828 A1 | 11/2010 |
| WO | WO 2011/001152 A1 | 1/2011 |
| WO | WO 2011/044186 A1 | 4/2011 |
| WO | WO 2012/013913 A1 | 2/2012 |
| WO | WO 2013/041865 A1 | 3/2013 |
| WO | WO 2013/169957 A1 | 11/2013 |
| WO | WO 2014/145992 A1 | 9/2014 |
| WO | WO 2014/182197 A1 | 11/2014 |
| WO | WO 2015/011450 A1 | 1/2015 |
| WO | WO 2015/136072 A1 | 9/2015 |
| WO | WO 2017/046198 A1 | 3/2017 |

OTHER PUBLICATIONS

Amstutz, et al., "In vitro display technologies: novel developments and applications," *Current Opinion in Biotechnology*, Aug. 2001, 12(4):400-405.

Arstila, et al., "A Direct Estimate of the Human αβ T Cell Receptor Diversity," *Science*, Oct. 1999, 286 (5441):958-961.

Boulter, et al., "Stable, soluble T-cell receptor molecules for crystallization and therapeutics," *Protein Engineering*, Sep. 2003, 16(9):707-711.

Chervin, et al., "Engineering higher affinity T cell receptors using a T cell display system," *Journal of Immunological Methods*, 2008, 339:175-184.

Garboczi, et al., "HLA-A2-peptide complexes: Refolding and crystallization of molecules expressed in *Escherichia coli* and complexed with single antigenic peptides," *PNAS*, Apr. 1992, 89:3429-3433.

Higuchi, et al., "Cell display library for gene cloning of variable regions of human antibodies to hepatitis B surface Antigen," *Journal of Immunological Methods*, Mar. 1997, 202(2):193-204.

Hoogenboom, et al., "Antibody phage display technology and its applications," Immunotechnology, Jun. 1998, 4(11):1-20.

Johnson et al., "Gene therapy with human and mouse T-cell receptors mediates cancer regression and targets normal tissues expressing cognate antigen," *Blood*, Jul. 16, 2009, 114(3):535-46.

Kessels, et al., "Changing T cell specificity by retroviral T cell receptor display," *PNAS*, Dec. 2000, 97(26): 14578-14583.

Kuball, J. et al., "Increasing functional avidity of TCR-redirected T cells by removing defined N-glycosylation sites in the TCR constant domain," *Journal of Experimental Medicine*, Feb. 16, 2009, 206(2):463-75.

O'Callaghan et al., "BirA Enzyme: Production and Application in the Study of Membrane Receptor-Ligand Interactions by Site-Specific Biotinylation," *Analytical Biochemistry*, Jan. 1, 1999, 266(1):9-15.

Pande, et al., "Phage display: Concept, innovations, applications and future," *Biotechnology Advances*, 2010, 28:849-858.

Pluckthun, et al., "In vitro selection and evolution of proteins," *Advances in Protein Chemistry*, 2001, 55:367-403.

Robins, et al., "Comprehensive assessment of T-cell receptor β-chain diversity in αβ T cells," Blood, Nov. 2009, 114(19):4099-4107.

Rosenberg et al., "Adoptive cell transfer: a clinical path to effective cancer immunotherapy," *Nature Reviews Cancer*, Apr. 2008, 8(4):299-308.

Samuelson, et al., "Display of proteins on bacteria," *Journal of Biotechnology*, Jun. 2002, 96(2):129-154.

Schlessinger, "SH2/SH3 signaling proteins," *Current Opinion in Genetics & Development*, Feb. 1994, (1):25-30.

(56) References Cited

OTHER PUBLICATIONS

Schmitz, et al., "Phage Display: A Molecular Tool for the Generation of Antibodies—A Review," *Placenta*, 2000, 21 (Supp A): S106-S112.
Shusta, et al., "Yeast polypeptide fusion surface display levels predict thermal stability and soluble secretion efficiency," *Journal of Molecular Biology*, 1999, 292:949-956.
Smith, "Filamentous fusion phage: novel expression vectors that display cloned antigens on the virion surface," *Science*, Jun. 1985, 228(4705):1315-1317.
Souriau and Hudson, "Recombinant antibodies for cancer diagnosis and therapy," *Expert Opinion on Biological Therapy*, 2001, 1(5):845-855.
Arden, B. et al. "Human T-cell receptor variable gene segment families," *Immunogenetics*, Oct. 1995, vol. 42, Issue 6, pp. 455-500.
Bridgeman, J. S. et al., "Structural and biophysical determinants of αβ T-cell antigen recognition," *Immunology*, Jan. 2012, vol. 135, Issue 1, pp. 9-18.
Busch and Pamer, "T Cell Affinity Maturation by Selective Expansion during Infection,"*Journal of Experimental Medicine*, Feb. 15, 1999, vol. 189, Issue 4, pp. 701-710.
Dunn, S.M. et al., "Directed evolution of human T cell receptor CDR2 residues by phage display dramatically enhances affinity for cognate peptide-MHC without increasing apparent cross-reactivity," *Protein Science*, Apr. 2006, vol. 15, Issue 4, pp. 710-721.
International Search Report and Written Opinion, PCT Application. No. PCT/EP/2016/071757, dated Dec. 16, 2016, 14 pages.
International Search Report and Written Opinion, PCT Application. No. PCT/EP/2016/071761, dated Dec. 22, 2016, 13 pages.
International Search Report and Written Opinion, PCT Application. No. PCT/EP/2016/071762, dated Dec. 9, 2016, 14 pages.
International Search Report and Written Opinion, PCT Application. No. PCT/EP/2016/071765, dated Nov. 23, 2016, 14 pages.
International Search Report and Written Opinion, PCT Application. No. PCT/EP/2016/071767, dated Jan. 2, 2017, 15 pages.
International Search Report and Written Opinion, PCT Application. No. PCT/EP/2016/071768, dated Jan. 31, 2017, 16 pages.
International Search Report and Written Opinion, PCT Application. No. PCT/EP/2016/071771, dated Dec. 12, 2016, 14 pages.
International Search Report and Written Opinion, PCT Application. No. PCT/EP/2016/071772, dated Jan. 3, 2017, 15 pages.
International Search Report and Written Opinion, PCT Application. No. PCT/EP2015/055293, dated Jun. 10, 2015, 9 pages.
Lefranc et al., "IMGT unique numbering for immunoglobulin and T cell receptor variable domains and Ig superfamily V-like domains," *Developmental & Comparative Immunology*, Jan. 2003, vol. 27, Issue 1, pp. 55-77.
Li, Y. et al., "Directed evolution of human T-cell receptors with picomolar affinities by phage display," *Nature Biotechnology*, Feb. 20, 2005, vol. 23, pp. 349-354.
Linnemann, C. et al. "High-throughput identification of antigen-specific TCRs by TCR gene capture," *Nature Medicine*, Oct. 13, 2013, 19 (11), pp. 1534-1541.
Malecek, K. et al., "Engineering improved T cell receptors using an alanine-scan guided T cell display selection system," *Journal of Immunological Methods*, vol. 392, Issues 1-2, Jun. 28, 2013, pp. 1-11.
Matsutani, T. et al., "Analysis of TCRAV and TCRBV Repertoires in Healthy Individuals by Microplate Hybridization Assay," *Human Immunology*, Aug.-Sep. 1997, vol. 56, Issues 1-2, pp. 57-69.
Oprea, M. et al., "Genetic Plasticity of V Genes Under Somatic Hypermutation: Statistical Analyses Using a New Resampling-Based Methodology," *Genome Research*, Dec. 1999, 9(12), pp. 1294-1304.
Ribas, A. and Koya, R.C., "Adoptive cell transfer of T-cell receptor-engineered lymphocytes: lessons from recent modeling." *Future Oncology*, 6(11), 2010, pp. 1671-1673.
Richman et al., "Display, engineering, and applications of antigen-specific T cell receptors," *Biomolecular Engineering*, vol. 24, Issue 4, Oct. 2007, pp. 361-373.
Robbins, P.F. et al., "Single and Dual Amino Acid Substitutions in TCR CDRs Can Enhance Antigen-Specific T Cell Functions," *The Journal of Immunology*, May 1, 2008, vol. 180, Issue 9, pp. 6116-6131.
Singer, M. and Berg, P., "Genes and Genomes: A Changing Perspective," 1991, University Science Books, Mill Valley, CA.
Stewart-Jones et al. "Rational development of high-affinity T-cell receptor-like antibodies," *Proceedings of the National Academy of Sciences*, Apr. 7, 2009, 106(14), pp. 5784-5788.
Stone, J.D. et al., "Chapter Eight—T Cell Receptor Engineering," *Methods in Enzymology*, vol. 503, 2012, pp. 189-222.
Walchli, S. et al., "A Practical Approach to T-Cell Receptor Cloning and Expression," PLoS ONE, Nov. 2011, vol. 6, Issue 11, e27930, pp. 1-11.
Yarilin, A.A., "Fundamentals of immunology", M.: Medicine, 1999, pp. 184-186.
Aggen et al., "Identification and engineering of human variable regions that allow expression of stable single-chain T cell receptors," *Protein Engineering, Design & Selection*, vol. 24, Issue 4, Apr. 2011, 361-372.
Buonpane et al, abstract only, "Characterization of T Cell Receptors Engineered for High Affinity Against Toxic Shock Syndrome Toxin-1," *Journal of Molecular Biology*, vol. 353, Issue 2, Oct. 21, 2005, pp. 308-321 Abstract only.
IMGT Home page, "The International Immunogenetics Information System," http://www/imgt.org, Mar. 31, 2017, 4 pages.
Panda and Ding, "Natural Antibodies Bridge Innate and Adaptive Immunity," *The Journal of Immunology*, vol. 194, Iss. 1, Jan. 1, 2015, pp. 13-20.
Quan, C. P. et al., "Different Dysregulations of the Natural Antibody Repertoire in Treated and Untreated HIV-1 Patients," *Journal of Autoimmunity*, vol. 17, Issue 1, Aug. 2001, pp. 81-87.
Weidanz et al., "Display of functional αβ single-chain T-cell receptor molecules on the surface of bacteriophage," Journal of Immunological Methods, vol. 221, Issues 1-2, Dec. 1998, pp. 59-76.
Zhou, Z.-H. et al., "The Broad Antibacterial Activity of the Natural Antibody Repertoire is Due to Polyreactive Antibodies," *Cell Host & Microbe*, vol. 1, pp. 51-61, Mar. 2007.

* cited by examiner

Schematic of cloning step used in library construction

Figure 2
General primer sequences used in library construction

| YOL22  | cattttcagggatagcaagc   | SEQ ID No: 1 |
|--------|------------------------|--------------|
| YOL237 | gagtctctcagctggtacacgg | SEQ ID No: 2 |
| YOL240 | agtgtggccttttgggtgtg   | SEQ ID No: 3 |
| YOL236 | ccgtgtaccagctgagagactc | SEQ ID No: 4 |
| YOL238 | gcgcgctgtgagaatagaaag  | SEQ ID No: 5 |
| YOL239 | cacacccaaaaggccacact   | SEQ ID No: 6 |

Figure 3
TRAV primers that may be used in library construction

| | | |
|---|---|---|
| TRAV1-1 | ggacaaagccttgagcagccctctg | SEQ ID No: 7 |
| TRAV1-2 | ggacaaaacattgaccagcccact | SEQ ID No: 8 |
| TRAV2 | gctcagtcagtggctcagccggaagat | SEQ ID No: 9 |
| TRAV3 | cttgctaagaccacccagcccatctccatggactcat | SEQ ID No: 10 |
| TRAV4 | ggagaggatgtggagcagagtcttttc | SEQ ID No: 11 |
| TRAV5 | agccaaaagatagaacagaattc | SEQ ID No: 12 |
| TRAV6 | gcccagtctgtgagccagcata | SEQ ID No: 13 |
| TRAV8-1 | gcccagtcggtgacccagctt | SEQ ID No: 14 |
| TRAV8-2/4 | gcccagtcagtgacccagcc | SEQ ID No: 15 |
| TRAV8-3 | gcccagtctgtgacccagcttgacagccaa | SEQ ID No: 16 |
| TRAV8-6 | acccagtcggtgacccagcttgatg | SEQ ID No: 17 |
| TRAV8-7 | ggaaattcagtgacccagatg | SEQ ID No: 18 |
| TRAV9-2 | aaaaaccaagtggagcagagtcctcagtccctgatca | SEQ ID No: 19 |
| TRAV10 | cggaaggaggtggagcaggatcctggacccttcaa | SEQ ID No: 20 |
| TRAV12-1 | cagaaggaggtggagcagaattc | SEQ ID No: 21 |
| TRAV12-2 | cagaaggaggtggagcaggatcctggacca | SEQ ID No: 22 |
| TRAV12-3 | ggagagaatgtggagcagcat | SEQ ID No: 23 |
| TRAV13-1 | ggagagagtgtggggctgcatc | SEQ ID No: 24 |
| TRAV13-2 | gcccagaagataactcaaacc | SEQ ID No: 25 |
| TRAV14/DV4 | gcccagagagtgactcagccc | SEQ ID No: 26 |
| TRAV16 | agtcaacagggagaagaggatcctca | SEQ ID No: 27 |
| TRAV17 | gctcagaaggtaactcaagcg | SEQ ID No: 28 |
| TRAV19 | gaagaccaggtgacgcagag | SEQ ID No: 29 |
| TRAV20 | aaacaggaggtgacgcagattcctg | SEQ ID No: 30 |
| TRAV21 | ggaatacaagtggagcagagtcctccag | SEQ ID No: 31 |
| TRAV22 | cagcagcaggtgaaacaaag | SEQ ID No: 32 |
| TRAV23/DV6 | atactgaacgtggaacaaagtcc | SEQ ID No: 33 |
| TRAV24 | ggacaacaggtaatgcaaattc | SEQ ID No: 34 |
| TRAV25 | gatgctaagaccacccagccccc | SEQ ID No: 35 |
| TRAV26-1 | gatgctaagaccacacagccaaatt | SEQ ID No: 36 |
| TRAV26-2 | acccagctgctggagcagagccc | SEQ ID No: 37 |
| TRAV27 | gaccagcaagttaagcaaaattc | SEQ ID No: 38 |
| TRAV29/DV5 | caacaaccagtgcagagtcctcaagccg | SEQ ID No: 39 |
| TRAV30 | agccaagaactggagcagagtcctcagtccttgatcg | SEQ ID No: 40 |
| TRAV34 | ggtcaacagctgaatcagag | SEQ ID No: 41 |
| TRAV35 | gaagacaaggtggtacaaagccctctatc | SEQ ID No: 42 |

Figure 3 (continued)

| TRAV36/DV7 | gcccagacagtcactcagtctc | SEQ ID No: 43 |
|---|---|---|
| TRAV38-1/2 | gagctgaaagtggaacaaaac | SEQ ID No: 44 |
| TRAV39 | agcaatteagtcaagcagacgggcca | SEQ ID No: 45 |
| TRAV40 | aaaaatgaagtggagcagagtcctcagaac | SEQ ID No: 46 |
| TRAV41 | ggacaaagccttgagcagccctctg | SEQ ID No: 47 |

Figure 4
TRBV primers that may be used in library construction

| TRBV2 | gaacctgaagtcacccagactcccagc | SEQ ID No: 48 |
|---|---|---|
| TRBV3-1 | gacacagctgtttcccagac | SEQ ID No: 49 |
| TRBV4-1 | gacactgaagttacccagacaccaaaac | SEQ ID No: 50 |
| TRBV4-2/3 | gaaacgggagttacgcagac | SEQ ID No: 51 |
| TRBV5-1 | aaggctggagtcactcaaactccaag | SEQ ID No: 52 |
| TRBV5-4 | gagactggagtcacccaaag | SEQ ID No: 53 |
| TRBV5-5/6/7 | gacgctggagtcacccaaag | SEQ ID No: 54 |
| TRBV6-4 | attgctgggatcacccaggc | SEQ ID No: 55 |
| TRBV6-1/2/3/5/6 | aatgctggtgtcactcagaccccaaaa | SEQ ID No: 56 |
| TRBV7-2 | ggagctggagtctcccagtcccccagta | SEQ ID No: 57 |
| TRBV7-3/4/6/7/8 | ggtgctggagtctcccag | SEQ ID No: 58 |
| TRBV7-9 | gatactggagtctcccagaac | SEQ ID No: 59 |
| TRBV9 | gattctggagtcacacaaacc | SEQ ID No: 60 |
| TRBV10-2/3 | gatgctggaatcacccagag | SEQ ID No: 61 |
| TRBV11-1 | gaagctgaagttgcccagtcc | SEQ ID No: 62 |
| TRBV11-2 | gaagctggagttgcccagtct | SEQ ID No: 63 |
| TRBV11-3 | gaagctggagtggttc | SEQ ID No: 64 |
| TRBV12-3/4 | gatgctggagttatccagtca | SEQ ID No: 65 |
| TRBV12-5 | gatgctagagtcacccagaca | SEQ ID No: 66 |
| TRBV13 | gctgctggagtcatccagtccccaagac | SEQ ID No: 67 |
| TRBV14 | gaagctggagttactcagttc | SEQ ID No: 68 |
| TRBV15 | gatgccatggtcatccagaacccaagatacca | SEQ ID No: 69 |
| TRBV16 | ggtgaagaagtcgcccagactccaaaacat | SEQ ID No: 70 |
| TRBV18 | aatgccggcgtcatgcag | SEQ ID No: 71 |
| TRBV19 | gatggtggaatcactcagtcc | SEQ ID No: 72 |
| TRBV20-1 | ggtgctgtcgtctctcaacat | SEQ ID No: 73 |
| TRBV23-1 | catgccaaagtcacacagactccagg | SEQ ID No: 74 |
| TRBV24-1 | gatgctgatgttacccagacc | SEQ ID No: 75 |
| TRBV25-1 | gaagctgacatctaccagac | SEQ ID No: 76 |
| TRBV27 | gaagcccaagtgacccaga | SEQ ID No: 77 |
| TRBV28 | gatgtgaaagtaacccagagc | SEQ ID No: 78 |
| TRBV29-1 | agtgctgtcatctctcaaaag | SEQ ID No: 79 |
| TRBV30 | tctcagactattcatcaatgg | SEQ ID No: 80 |

Figure 5
A) Initial ELISA screening results from panning the library of Example 5 with two different peptide-HLA complexes. B) Further specificity testing of TCRs from positive ELISA clones obtained from the library
A)
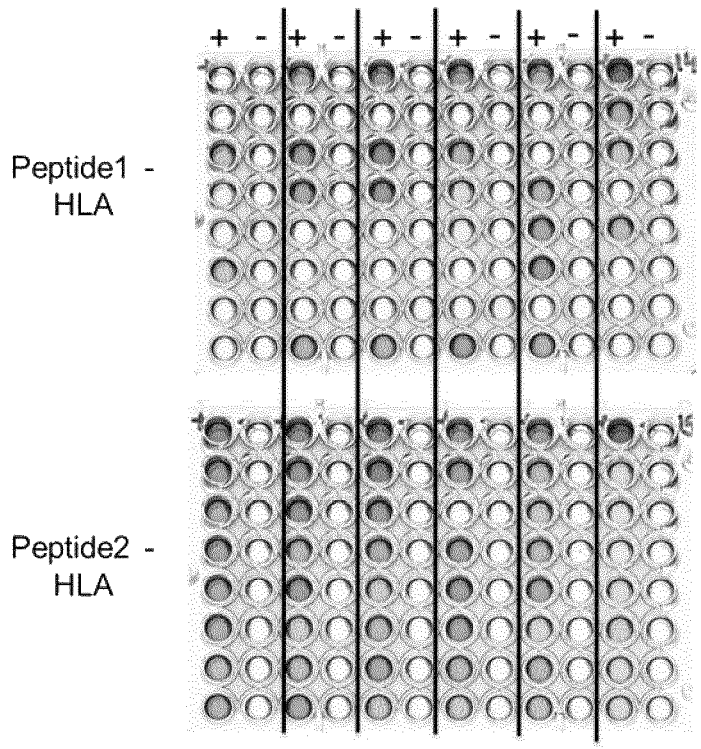
Peptide1 - HLA
Peptide2 - HLA
B)
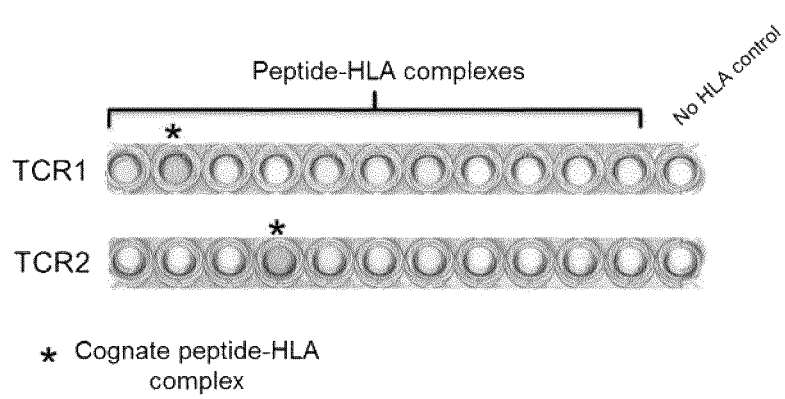
* Cognate peptide-HLA complex

Figure 6
A) Initial ELISA screening results from panning the comparative library of Example 5 with two different peptide-HLA complexes. B) Further specificity testing of TCRs from positive ELISA clones obtained from the library
A)
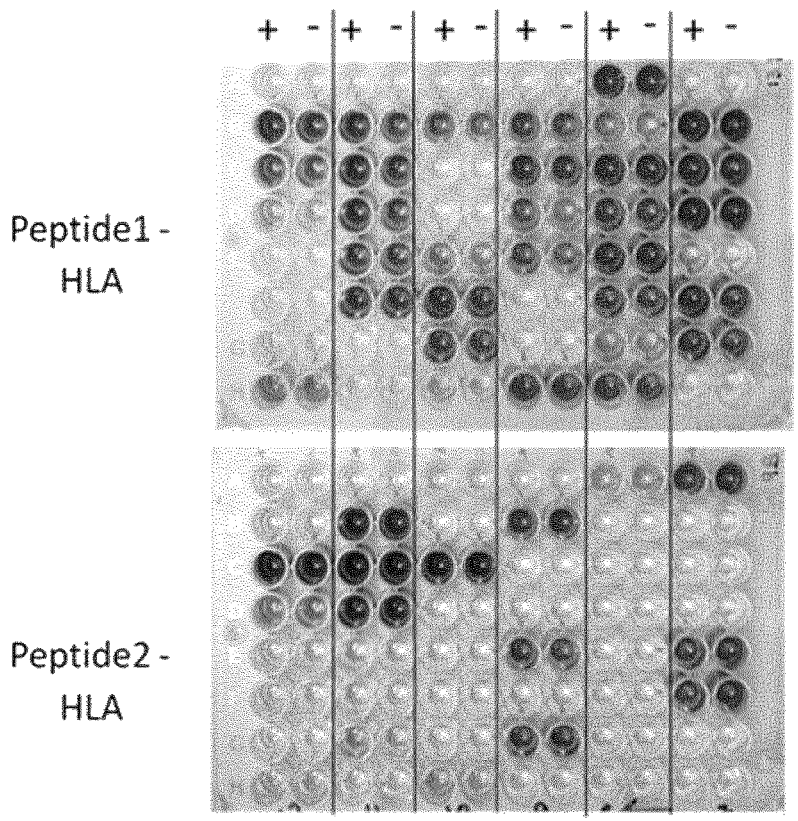
B)
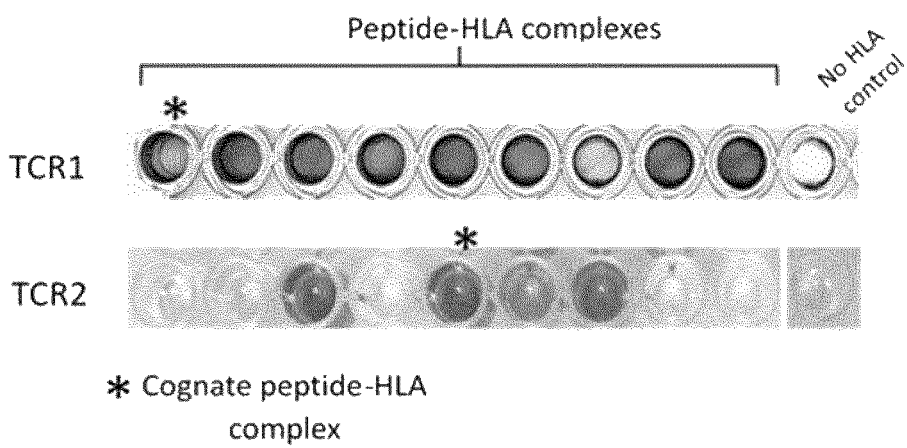
✱ Cognate peptide-HLA complex

Figure 7
A) Initial ELISA screening results from panning the library of Example 6 with two different peptide-HLA complexes. B) Further specificity testing of TCRs from positive ELISA clones obtained from the library
A)
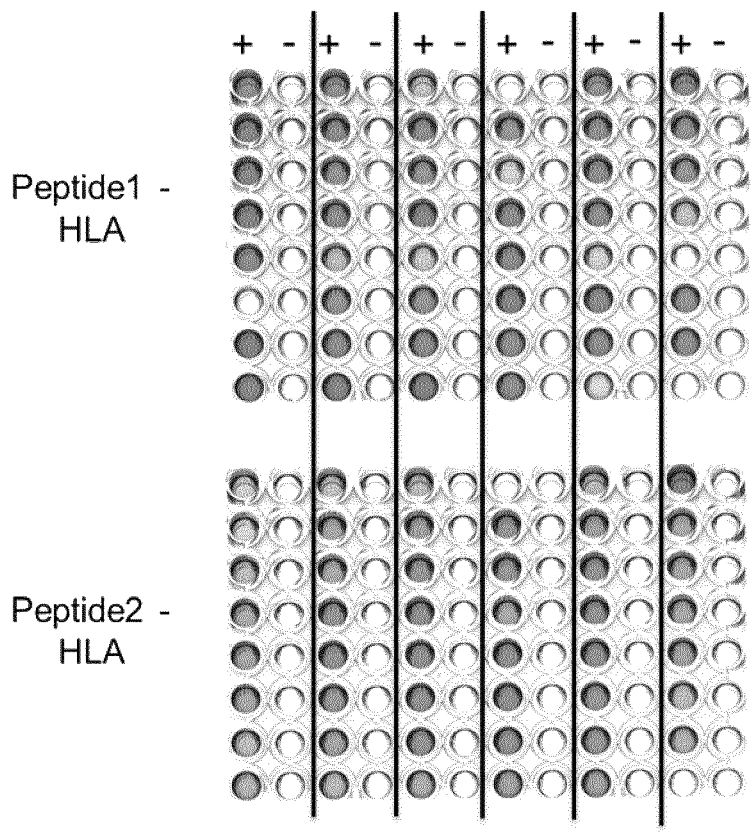
B)
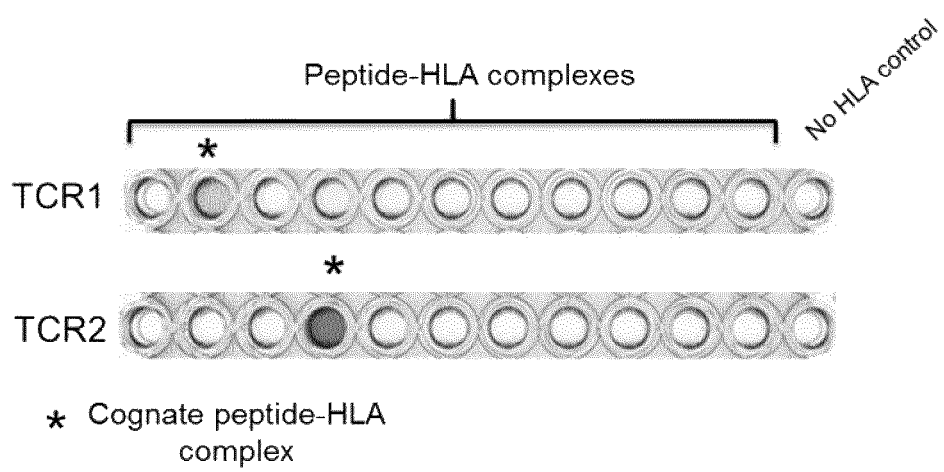

Figure 8
A) Initial ELISA screening results from panning the library of Example 7 with a peptide-HLA complexes. B) Further specificity testing of a TCR from a positive ELISA clone obtained from the library
A)
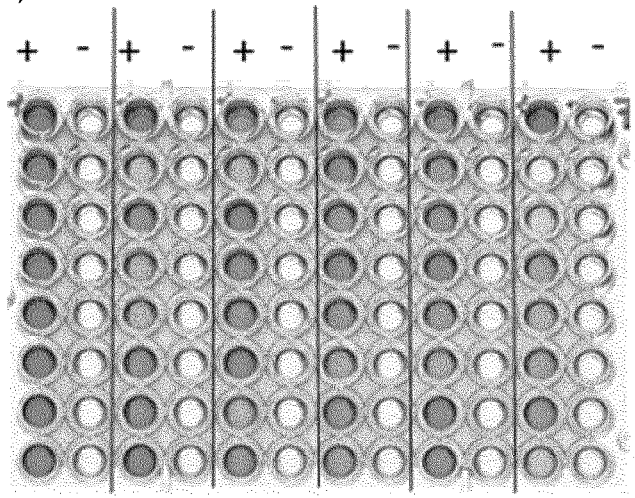
B)
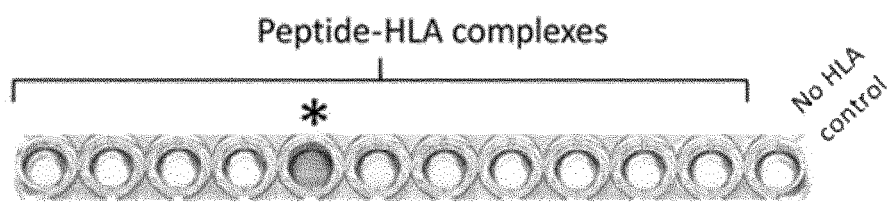
* Cognate peptide-HLA complex

Figure 9
A) Initial ELISA screening results from panning the library of Example 8 with a peptide-HLA complex. B) Further specificity testing of TCRs from ELISA positive clones obtained from the library
A)
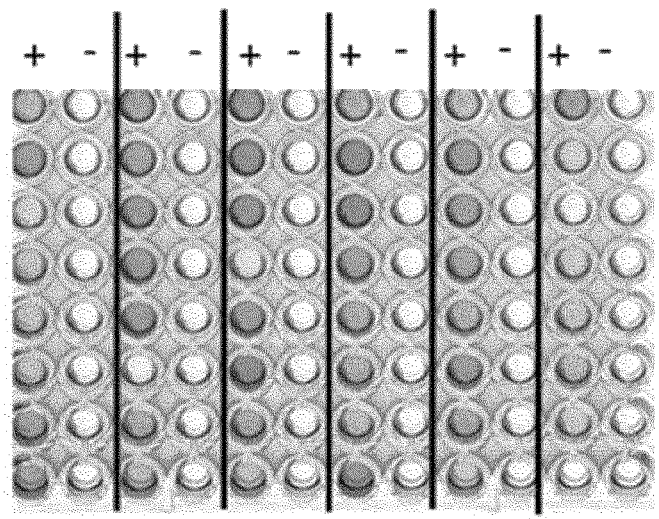
B)
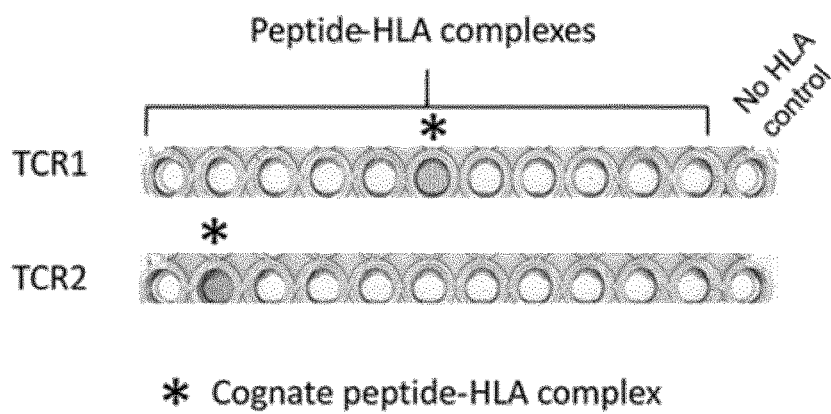
* Cognate peptide-HLA complex

Figure 10
A) Initial ELISA screening results from panning the library of Example 9 with a peptide-HLA complex. B) Further specificity testing of TCRs from ELISA positive clones obtained from the library
A)
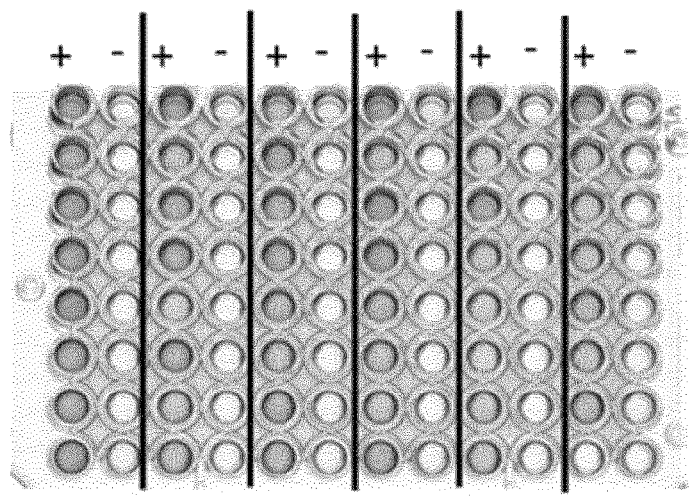
B)
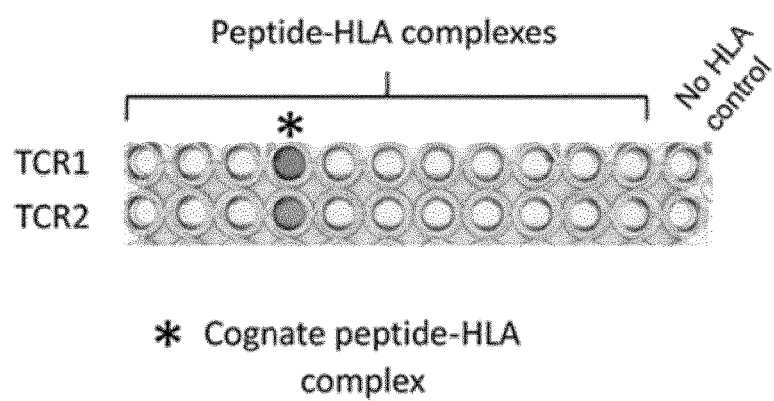
* Cognate peptide-HLA complex

Figure 11
A) Initial ELISA screening results from panning the libraries of Example 10 with two peptide-HLA complexes. B) Further specificity testing of TCRs from ELISA positive clones obtained from the library
A)
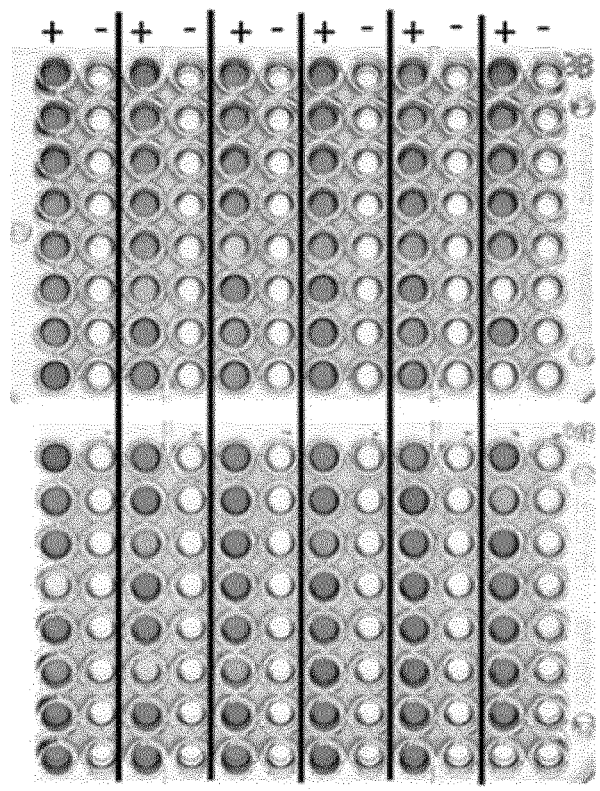
B)
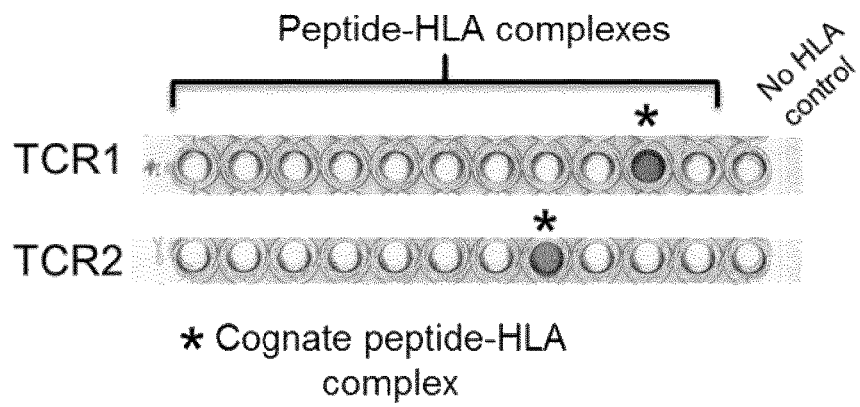

Figure 12
A) Initial ELISA screening results from panning the comparative libraries of Example 10 with two peptide-HLA complexes. B) Further specificity testing of TCRs from ELISA positive clones obtained from the library
A)
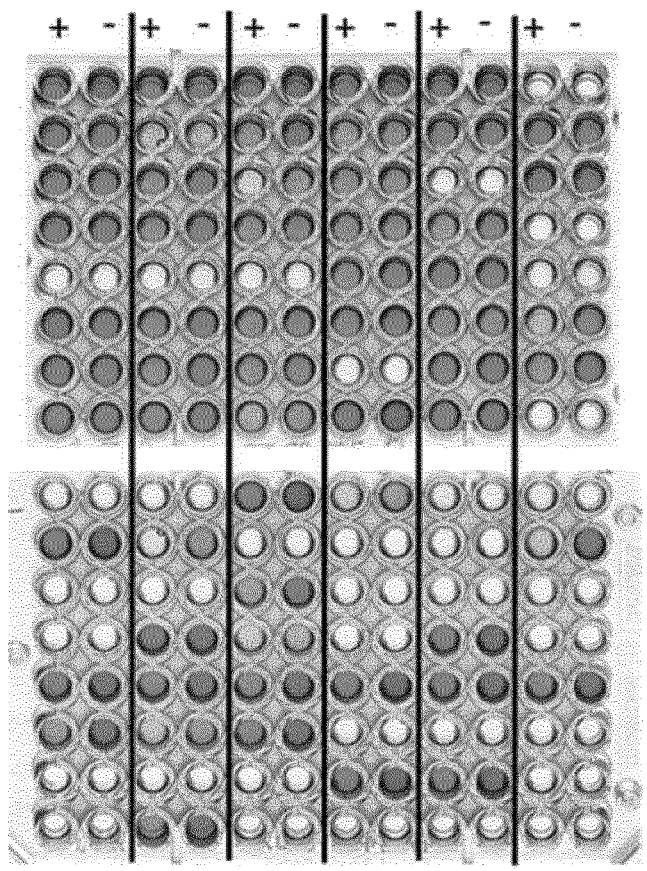
B)
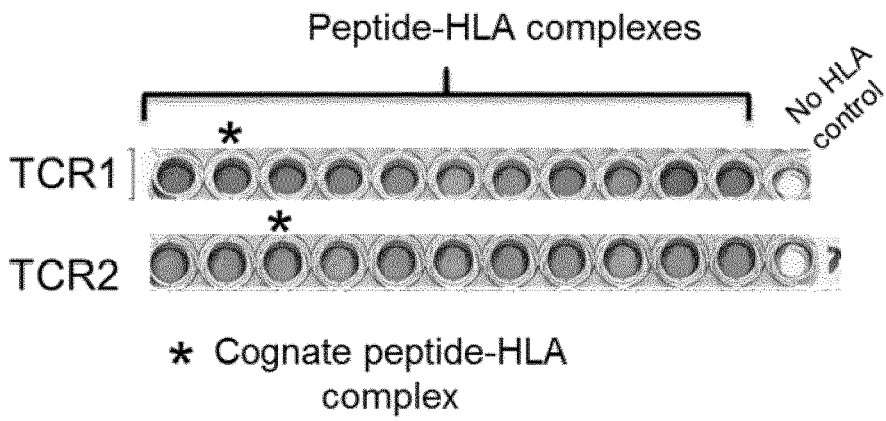
\* Cognate peptide-HLA complex ELISA specificity testing of TCRs from ELISA positive clones obtained from the library of Example 11

Example Biacore data for TCRs obtained from libraries of the invention

SEQUENCE LISTING

<160> NUMBER OF SEQ ID NOS: 80

<210> SEQ ID NO 1
<211> LENGTH: 20
<212> TYPE: DNA
<213> ORGANISM: Artificial Sequence
<220> FEATURE:
<223> OTHER INFORMATION: YOL22 Primer

<400> SEQUENCE: 1
cattttcagg gatagcaagc              20

<210> SEQ ID NO 2
<211> LENGTH: 22
<212> TYPE: DNA
<213> ORGANISM: Artificial Sequence

```
<220> FEATURE:
<223> OTHER INFORMATION: YOL237 Primer

<400> SEQUENCE: 2
gagtctctca gctggtacac gg                                          22

<210> SEQ ID NO 3
<211> LENGTH: 20
<212> TYPE: DNA
<213> ORGANISM: Artificial Sequence
<220> FEATURE:
<223> OTHER INFORMATION: YOL240 Primer

<400> SEQUENCE: 3
agtgtggcct tttgggtgtg                                             20

<210> SEQ ID NO 4
<211> LENGTH: 22
<212> TYPE: DNA
<213> ORGANISM: Artificial Sequence
<220> FEATURE:
<223> OTHER INFORMATION: YOL236 Primer

<400> SEQUENCE: 4
ccgtgtacca gctgagagac tc                                          22

<210> SEQ ID NO 5
<211> LENGTH: 21
<212> TYPE: DNA
<213> ORGANISM: Artificial Sequence
<220> FEATURE:
<223> OTHER INFORMATION: YOL238 Primer

<400> SEQUENCE: 5
gcgcgctgtg agaatagaaa g                                           21

<210> SEQ ID NO 6
<211> LENGTH: 20
<212> TYPE: DNA
<213> ORGANISM: Artificial Sequence
<220> FEATURE:
<223> OTHER INFORMATION: YOL239 Primer

<400> SEQUENCE: 6
cacacccaaa aggccacact                                             20

<210> SEQ ID NO 7
<211> LENGTH: 25
<212> TYPE: DNA
<213> ORGANISM: Artificial Sequence
<220> FEATURE:
<223> OTHER INFORMATION: TRAV1-1 Primer

<400> SEQUENCE: 7
ggacaaagcc ttgagcagcc ctctg                                       25

<210> SEQ ID NO 8
<211> LENGTH: 24
<212> TYPE: DNA
<213> ORGANISM: Artificial Sequence
<220> FEATURE:
<223> OTHER INFORMATION: TRAV1-2 Primer

<400> SEQUENCE: 8
ggacaaaaca ttgaccagcc cact                                        24
```

<210> SEQ ID NO 9
<211> LENGTH: 27
<212> TYPE: DNA
<213> ORGANISM: Artificial Sequence
<220> FEATURE:
<223> OTHER INFORMATION: TRAV2 Primer

<400> SEQUENCE: 9
gctcagtcag tggctcagcc ggaagat         27

<210> SEQ ID NO 10
<211> LENGTH: 37
<212> TYPE: DNA
<213> ORGANISM: Artificial Sequence
<220> FEATURE:
<223> OTHER INFORMATION: TRAV3 Primer

<400> SEQUENCE: 10
cttgctaaga ccacccagcc catctccatg gactcat         37

<210> SEQ ID NO 11
<211> LENGTH: 27
<212> TYPE: DNA
<213> ORGANISM: Artificial Sequence
<220> FEATURE:
<223> OTHER INFORMATION: TRAV4 Primer

<400> SEQUENCE: 11
ggagaggatg tggagcagag tcttttc         27

<210> SEQ ID NO 12
<211> LENGTH: 23
<212> TYPE: DNA
<213> ORGANISM: Artificial Sequence
<220> FEATURE:
<223> OTHER INFORMATION: TRAV5 Primer

<400> SEQUENCE: 12
agccaaaaga tagaacagaa ttc         23

<210> SEQ ID NO 13
<211> LENGTH: 22
<212> TYPE: DNA
<213> ORGANISM: Artificial Sequence
<220> FEATURE:
<223> OTHER INFORMATION: TRAV6 Primer

<400> SEQUENCE: 13
gcccagtctg tgagccagca ta         22

<210> SEQ ID NO 14
<211> LENGTH: 21
<212> TYPE: DNA
<213> ORGANISM: Artificial Sequence
<220> FEATURE:
<223> OTHER INFORMATION: TRAV8-1 Primer

<400> SEQUENCE: 14
gcccagtcgg tgacccagct t         21

<210> SEQ ID NO 15
<211> LENGTH: 20
<212> TYPE: DNA
<213> ORGANISM: Artificial Sequence
<220> FEATURE:
<223> OTHER INFORMATION: TRAV8-2/4 Primer

<400> SEQUENCE: 15
gcccagtcag tgacccagcc                                                 20

<210> SEQ ID NO 16
<211> LENGTH: 30
<212> TYPE: DNA
<213> ORGANISM: Artificial Sequence
<220> FEATURE:
<223> OTHER INFORMATION: TRAV8-3 Primer

<400> SEQUENCE: 16
gcccagtctg tgacccagct tgacagccaa                                      30

<210> SEQ ID NO 17
<211> LENGTH: 25
<212> TYPE: DNA
<213> ORGANISM: Artificial Sequence
<220> FEATURE:
<223> OTHER INFORMATION: TRAV8-6 Primer

<400> SEQUENCE: 17
acccagtcgg tgacccagct tgatg                                           25

<210> SEQ ID NO 18
<211> LENGTH: 21
<212> TYPE: DNA
<213> ORGANISM: Artificial Sequence
<220> FEATURE:
<223> OTHER INFORMATION: TRAV8-7 Primer

<400> SEQUENCE: 18
ggaaattcag tgacccagat g                                               21

<210> SEQ ID NO 19
<211> LENGTH: 37
<212> TYPE: DNA
<213> ORGANISM: Artificial Sequence
<220> FEATURE:
<223> OTHER INFORMATION: TRAV9-2 Primer

<400> SEQUENCE: 19
aaaaaccaag tggagcagag tcctcagtcc ctgatca                              37

<210> SEQ ID NO 20
<211> LENGTH: 35
<212> TYPE: DNA
<213> ORGANISM: Artificial Sequence
<220> FEATURE:
<223> OTHER INFORMATION: TRAV10 Primer

<400> SEQUENCE: 20
cggaaggagg tggagcagga tcctggaccc ttcaa                                35

<210> SEQ ID NO 21
<211> LENGTH: 23
<212> TYPE: DNA
<213> ORGANISM: Artificial Sequence
<220> FEATURE:
<223> OTHER INFORMATION: TRAV12-1 Primer

<400> SEQUENCE: 21
cagaaggagg tggagcagaa ttc                                             23

<210> SEQ ID NO 22

<210> SEQ ID NO 22
<211> LENGTH: 30
<212> TYPE: DNA
<213> ORGANISM: Artificial Sequence
<220> FEATURE:
<223> OTHER INFORMATION: TRAV12-2 Primer

<400> SEQUENCE: 22
cagaaggagg tggagcagga tcctggacca                           30

<210> SEQ ID NO 23
<211> LENGTH: 21
<212> TYPE: DNA
<213> ORGANISM: Artificial Sequence
<220> FEATURE:
<223> OTHER INFORMATION: TRAV12-3

<400> SEQUENCE: 23
ggagagaatg tggagcagca t                                    21

<210> SEQ ID NO 24
<211> LENGTH: 22
<212> TYPE: DNA
<213> ORGANISM: Artificial Sequence
<220> FEATURE:
<223> OTHER INFORMATION: TRAV13-1 Primer

<400> SEQUENCE: 24
ggagagagtg tggggctgca tc                                   22

<210> SEQ ID NO 25
<211> LENGTH: 21
<212> TYPE: DNA
<213> ORGANISM: Artificial Sequence
<220> FEATURE:
<223> OTHER INFORMATION: TRAV13-2 Primer

<400> SEQUENCE: 25
gcccagaaga taactcaaac c                                    21

<210> SEQ ID NO 26
<211> LENGTH: 21
<212> TYPE: DNA
<213> ORGANISM: Artificial Sequence
<220> FEATURE:
<223> OTHER INFORMATION: TRAV14/DV4 Primer

<400> SEQUENCE: 26
gcccagagag tgactcagcc c                                    21

<210> SEQ ID NO 27
<211> LENGTH: 26
<212> TYPE: DNA
<213> ORGANISM: Artificial Sequence
<220> FEATURE:
<223> OTHER INFORMATION: TRAV16

<400> SEQUENCE: 27
agtcaacagg gagaagagga tcctca                               26

<210> SEQ ID NO 28
<211> LENGTH: 21
<212> TYPE: DNA
<213> ORGANISM: Artificial Sequence
<220> FEATURE:
<223> OTHER INFORMATION: TRAV17 Primer

<400> SEQUENCE: 28
gctcagaagg taactcaagc g                                              21

<210> SEQ ID NO 29
<211> LENGTH: 20
<212> TYPE: DNA
<213> ORGANISM: Artificial Sequence
<220> FEATURE:
<223> OTHER INFORMATION: TRAV19 Primer

<400> SEQUENCE: 29
gaagaccagg tgacgcagag                                                20

<210> SEQ ID NO 30
<211> LENGTH: 25
<212> TYPE: DNA
<213> ORGANISM: Artificial Sequence
<220> FEATURE:
<223> OTHER INFORMATION: TRAV20 Primer

<400> SEQUENCE: 30
aaacaggagg tgacgcagat tcctg                                          25

<210> SEQ ID NO 31
<211> LENGTH: 28
<212> TYPE: DNA
<213> ORGANISM: Artificial Sequence
<220> FEATURE:
<223> OTHER INFORMATION: TRAV21 Primer

<400> SEQUENCE: 31
ggaatacaag tggagcagag tcctccag                                       28

<210> SEQ ID NO 32
<211> LENGTH: 20
<212> TYPE: DNA
<213> ORGANISM: Artificial Sequence
<220> FEATURE:
<223> OTHER INFORMATION: TRAV22 Primer

<400> SEQUENCE: 32
cagcagcagg tgaaacaaag                                                20

<210> SEQ ID NO 33
<211> LENGTH: 23
<212> TYPE: DNA
<213> ORGANISM: Artificial Sequence
<220> FEATURE:
<223> OTHER INFORMATION: TRAV23/DV6 Primer

<400> SEQUENCE: 33
atactgaacg tggaacaaag tcc                                            23

<210> SEQ ID NO 34
<211> LENGTH: 22
<212> TYPE: DNA
<213> ORGANISM: Artificial Sequence
<220> FEATURE:
<223> OTHER INFORMATION: TRAV24 Primer

<400> SEQUENCE: 34
ggacaacagg taatgcaaat tc                                             22

<210> SEQ ID NO 35
<211> LENGTH: 23
<212> TYPE: DNA

```
<213> ORGANISM: Artificial Sequence
<220> FEATURE:
<223> OTHER INFORMATION: TRAV25 Primer

<400> SEQUENCE: 35
gatgctaaga ccacccagcc ccc                                            23

<210> SEQ ID NO 36
<211> LENGTH: 25
<212> TYPE: DNA
<213> ORGANISM: Artificial Sequence
<220> FEATURE:
<223> OTHER INFORMATION: TRAV26-1 Primer

<400> SEQUENCE: 36
gatgctaaga ccacacagcc aaatt                                          25

<210> SEQ ID NO 37
<211> LENGTH: 23
<212> TYPE: DNA
<213> ORGANISM: Artificial Sequence
<220> FEATURE:
<223> OTHER INFORMATION: TRAV26-2 Primer

<400> SEQUENCE: 37
acccagctgc tggagcagag ccc                                            23

<210> SEQ ID NO 38
<211> LENGTH: 23
<212> TYPE: DNA
<213> ORGANISM: Artificial Sequence
<220> FEATURE:
<223> OTHER INFORMATION: TRAV27 Primer

<400> SEQUENCE: 38
gaccagcaag ttaagcaaaa ttc                                            23

<210> SEQ ID NO 39
<211> LENGTH: 28
<212> TYPE: DNA
<213> ORGANISM: Artificial Sequence
<220> FEATURE:
<223> OTHER INFORMATION: TRAV29/DV5 Primer

<400> SEQUENCE: 39
caacaaccag tgcagagtcc tcaagccg                                       28

<210> SEQ ID NO 40
<211> LENGTH: 37
<212> TYPE: DNA
<213> ORGANISM: Artificial Sequence
<220> FEATURE:
<223> OTHER INFORMATION: TRAV30 Primer

<400> SEQUENCE: 40
agccaagaac tggagcagag tcctcagtcc ttgatcg                             37

<210> SEQ ID NO 41
<211> LENGTH: 20
<212> TYPE: DNA
<213> ORGANISM: Artificial Sequence
<220> FEATURE:
<223> OTHER INFORMATION: TRAV34 Primer

<400> SEQUENCE: 41
ggtcaacagc tgaatcagag                                                20
```

<210> SEQ ID NO 42
<211> LENGTH: 29
<212> TYPE: DNA
<213> ORGANISM: Artificial Sequence
<220> FEATURE:
<223> OTHER INFORMATION: TRAV35 Primer

<400> SEQUENCE: 42
gaagacaagg tggtacaaag ccctctatc                              29

<210> SEQ ID NO 43
<211> LENGTH: 22
<212> TYPE: DNA
<213> ORGANISM: Artificial Sequence
<220> FEATURE:
<223> OTHER INFORMATION: TRAV36/DV7 Primer

<400> SEQUENCE: 43
gcccagacag tcactcagtc tc                                     22

<210> SEQ ID NO 44
<211> LENGTH: 21
<212> TYPE: DNA
<213> ORGANISM: Artificial Sequence
<220> FEATURE:
<223> OTHER INFORMATION: TRAV38-1/2 Primer

<400> SEQUENCE: 44
gagctgaaag tggaacaaaa c                                      21

<210> SEQ ID NO 45
<211> LENGTH: 26
<212> TYPE: DNA
<213> ORGANISM: Artificial Sequence
<220> FEATURE:
<223> OTHER INFORMATION: TRAV39 Primer

<400> SEQUENCE: 45
agcaattcag tcaagcagac gggcca                                 26

<210> SEQ ID NO 46
<211> LENGTH: 30
<212> TYPE: DNA
<213> ORGANISM: Artificial Sequence
<220> FEATURE:
<223> OTHER INFORMATION: TRAV40 Primer

<400> SEQUENCE: 46
aaaaatgaag tggagcagag tcctcagaac                             30

<210> SEQ ID NO 47
<211> LENGTH: 25
<212> TYPE: DNA
<213> ORGANISM: Artificial Sequence
<220> FEATURE:
<223> OTHER INFORMATION: TRAV41 Primer

<400> SEQUENCE: 47
ggacaaagcc ttgagcagcc ctctg                                  25

<210> SEQ ID NO 48
<211> LENGTH: 27
<212> TYPE: DNA
<213> ORGANISM: Artificial Sequence
<220> FEATURE:

<223> OTHER INFORMATION: TRBV2 Primer

<400> SEQUENCE: 48
gaacctgaag tcacccagac tcccagc                                    27

<210> SEQ ID NO 49
<211> LENGTH: 20
<212> TYPE: DNA
<213> ORGANISM: Artificial Sequence
<220> FEATURE:
<223> OTHER INFORMATION: TRBV3-1 Primer

<400> SEQUENCE: 49
gacacagctg tttcccagac                                            20

<210> SEQ ID NO 50
<211> LENGTH: 28
<212> TYPE: DNA
<213> ORGANISM: Artificial Sequence
<220> FEATURE:
<223> OTHER INFORMATION: TRBV4-1 Primer

<400> SEQUENCE: 50
gacactgaag ttacccagac accaaaac                                   28

<210> SEQ ID NO 51
<211> LENGTH: 20
<212> TYPE: DNA
<213> ORGANISM: Artificial Sequence
<220> FEATURE:
<223> OTHER INFORMATION: TRBV4-2/3 Primer

<400> SEQUENCE: 51
gaaacgggag ttacgcagac                                            20

<210> SEQ ID NO 52
<211> LENGTH: 26
<212> TYPE: DNA
<213> ORGANISM: Artificial Sequence
<220> FEATURE:
<223> OTHER INFORMATION: TRBV5-1 Primer

<400> SEQUENCE: 52
aaggctggag tcactcaaac tccaag                                     26

<210> SEQ ID NO 53
<211> LENGTH: 20
<212> TYPE: DNA
<213> ORGANISM: Artificial Sequence
<220> FEATURE:
<223> OTHER INFORMATION: TRBV5-4 Primer

<400> SEQUENCE: 53
gagactggag tcacccaaag                                            20

<210> SEQ ID NO 54
<211> LENGTH: 20
<212> TYPE: DNA
<213> ORGANISM: Artificial Sequence
<220> FEATURE:
<223> OTHER INFORMATION: TRBV5-5/6/7 Primer

<400> SEQUENCE: 54
gacgctggag tcacccaaag                                            20

```
<210> SEQ ID NO 55
<211> LENGTH: 20
<212> TYPE: DNA
<213> ORGANISM: Artificial Sequence
<220> FEATURE:
<223> OTHER INFORMATION: TRBV6-4 Primer

<400> SEQUENCE: 55
attgctggga tcacccaggc                                                 20

<210> SEQ ID NO 56
<211> LENGTH: 27
<212> TYPE: DNA
<213> ORGANISM: Artificial Sequence
<220> FEATURE:
<223> OTHER INFORMATION: TRBV6-1/2/3/5/6 Primer

<400> SEQUENCE: 56
aatgctggtg tcactcagac cccaaaa                                         27

<210> SEQ ID NO 57
<211> LENGTH: 28
<212> TYPE: DNA
<213> ORGANISM: Artificial Sequence
<220> FEATURE:
<223> OTHER INFORMATION: TRBV7-2 Primer

<400> SEQUENCE: 57
ggagctggag tctcccagtc ccccagta                                        28

<210> SEQ ID NO 58
<211> LENGTH: 18
<212> TYPE: DNA
<213> ORGANISM: Artificial Sequence
<220> FEATURE:
<223> OTHER INFORMATION: TRBV7-3/4/6/7/8 Primer

<400> SEQUENCE: 58
ggtgctggag tctcccag                                                   18

<210> SEQ ID NO 59
<211> LENGTH: 21
<212> TYPE: DNA
<213> ORGANISM: Artificial Sequence
<220> FEATURE:
<223> OTHER INFORMATION: TRBV7-9 Primer

<400> SEQUENCE: 59
gatactggag tctcccagaa c                                               21

<210> SEQ ID NO 60
<211> LENGTH: 21
<212> TYPE: DNA
<213> ORGANISM: Artificial Sequence
<220> FEATURE:
<223> OTHER INFORMATION: TRBV9 Primer

<400> SEQUENCE: 60
gattctggag tcacacaaac c                                               21

<210> SEQ ID NO 61
<211> LENGTH: 20
<212> TYPE: DNA
<213> ORGANISM: Artificial Sequence
<220> FEATURE:
<223> OTHER INFORMATION: TRBV10-2/3 Primer
```

<400> SEQUENCE: 61
gatgctggaa tcacccagag                                              20

<210> SEQ ID NO 62
<211> LENGTH: 21
<212> TYPE: DNA
<213> ORGANISM: Artificial Sequence
<220> FEATURE:
<223> OTHER INFORMATION: TRBV11-1 Primer

<400> SEQUENCE: 62
gaagctgaag ttgcccagtc c                                            21

<210> SEQ ID NO 63
<211> LENGTH: 21
<212> TYPE: DNA
<213> ORGANISM: Artificial Sequence
<220> FEATURE:
<223> OTHER INFORMATION: TRBV11-2 Primer

<400> SEQUENCE: 63
gaagctggag ttgcccagtc t                                            21

<210> SEQ ID NO 64
<211> LENGTH: 16
<212> TYPE: DNA
<213> ORGANISM: Artificial Sequence
<220> FEATURE:
<223> OTHER INFORMATION: TRBV11-3 Primer

<400> SEQUENCE: 64
gaagctggag tggttc                                                  16

<210> SEQ ID NO 65
<211> LENGTH: 21
<212> TYPE: DNA
<213> ORGANISM: Artificial Sequence
<220> FEATURE:
<223> OTHER INFORMATION: TRBV12-3/4 Primer

<400> SEQUENCE: 65
gatgctggag ttatccagtc a                                            21

<210> SEQ ID NO 66
<211> LENGTH: 21
<212> TYPE: DNA
<213> ORGANISM: Artificial Sequence
<220> FEATURE:
<223> OTHER INFORMATION: TRBV12-5 Primer

<400> SEQUENCE: 66
gatgctagag tcacccagac a                                            21

<210> SEQ ID NO 67
<211> LENGTH: 28
<212> TYPE: DNA
<213> ORGANISM: Artificial Sequence
<220> FEATURE:
<223> OTHER INFORMATION: TRBV13 Primer

<400> SEQUENCE: 67
gctgctggag tcatccagtc cccaagac                                     28

<210> SEQ ID NO 68
<211> LENGTH: 21

```
<212> TYPE: DNA
<213> ORGANISM: Artificial Sequence
<220> FEATURE:
<223> OTHER INFORMATION: TRBV14 Primer

<400> SEQUENCE: 68
gaagctggag ttactcagtt c                                           21

<210> SEQ ID NO 69
<211> LENGTH: 32
<212> TYPE: DNA
<213> ORGANISM: Artificial Sequence
<220> FEATURE:
<223> OTHER INFORMATION: TRBV15 Primer

<400> SEQUENCE: 69
gatgccatgg tcatccagaa cccaagatac ca                               32

<210> SEQ ID NO 70
<211> LENGTH: 30
<212> TYPE: DNA
<213> ORGANISM: Artificial Sequence
<220> FEATURE:
<223> OTHER INFORMATION: TRBV16 Primer

<400> SEQUENCE: 70
ggtgaagaag tcgcccagac tccaaaacat                                  30

<210> SEQ ID NO 71
<211> LENGTH: 18
<212> TYPE: DNA
<213> ORGANISM: Artificial Sequence
<220> FEATURE:
<223> OTHER INFORMATION: TRBV18 Primer

<400> SEQUENCE: 71
aatgccggcg tcatgcag                                               18

<210> SEQ ID NO 72
<211> LENGTH: 21
<212> TYPE: DNA
<213> ORGANISM: Artificial Sequence
<220> FEATURE:
<223> OTHER INFORMATION: TRBV19 Primer

<400> SEQUENCE: 72
gatggtggaa tcactcagtc c                                           21

<210> SEQ ID NO 73
<211> LENGTH: 21
<212> TYPE: DNA
<213> ORGANISM: Artificial Sequence
<220> FEATURE:
<223> OTHER INFORMATION: TRBV20-1 Primer

<400> SEQUENCE: 73
ggtgctgtcg tctctcaaca t                                           21

<210> SEQ ID NO 74
<211> LENGTH: 26
<212> TYPE: DNA
<213> ORGANISM: Artificial Sequence
<220> FEATURE:
<223> OTHER INFORMATION: TRBV23-1 Primer

<400> SEQUENCE: 74
```
catgccaaag tcacacagac tccagg					26

<210> SEQ ID NO 75
<211> LENGTH: 21
<212> TYPE: DNA
<213> ORGANISM: Artificial Sequence
<220> FEATURE:
<223> OTHER INFORMATION: TRBV24-1 Primer

<400> SEQUENCE: 75
gatgctgatg ttacccagac c					21

<210> SEQ ID NO 76
<211> LENGTH: 20
<212> TYPE: DNA
<213> ORGANISM: Artificial Sequence
<220> FEATURE:
<223> OTHER INFORMATION: TRBV25-1 Primer

<400> SEQUENCE: 76
gaagctgaca tctaccagac					20

<210> SEQ ID NO 77
<211> LENGTH: 19
<212> TYPE: DNA
<213> ORGANISM: Artificial Sequence
<220> FEATURE:
<223> OTHER INFORMATION: TRBV27 Primer

<400> SEQUENCE: 77
gaagcccaag tgacccaga					19

<210> SEQ ID NO 78
<211> LENGTH: 21
<212> TYPE: DNA
<213> ORGANISM: Artificial Sequence
<220> FEATURE:
<223> OTHER INFORMATION: TRBV28 Primer

<400> SEQUENCE: 78
gatgtgaaag taacccagag c					21

<210> SEQ ID NO 79
<211> LENGTH: 21
<212> TYPE: DNA
<213> ORGANISM: Artificial Sequence
<220> FEATURE:
<223> OTHER INFORMATION: TRBV29-1 Primer

<400> SEQUENCE: 79
agtgctgtca tctctcaaaa g					21

<210> SEQ ID NO 80
<211> LENGTH: 21
<212> TYPE: DNA
<213> ORGANISM: Artificial Sequence
<220> FEATURE:
<223> OTHER INFORMATION: TRBV30 Primer

<400> SEQUENCE: 80
tctcagacta ttcatcaatg g					21

TCR LIBRARIES

CROSS-REFERENCE TO RELATED APPLICATIONS

This application is the National Stage of International Application No. PCT/EP2016/071761, filed Sep. 15, 2016, which claims the benefit of and priority to Great Britain Patent Application Serial No. 1516277.9, filed on Sep. 15, 2015, the contents of which are incorporated by reference in their entirety.

The present invention relates to a library of particles displaying a plurality of T cell receptors (TCRs), wherein the plurality of TCRs: i) consists essentially of TCRs comprising an alpha chain comprising an alpha chain variable domain and beta chain comprising a beta chain variable domain that does not comprise one or more of a TRBV5-1, 5-3, 5-4, 5-5, 5-6, 5-7 or 5-8 gene product; ii) comprises more than one TRAV gene product and/or more than one TRBV gene product; and iii) does not consist essentially of TCRs comprising a TRAV12-2 gene product from a natural repertoire and a TRBV6 gene product from a natural repertoire and TCRs comprising a TRAV21 gene product from a natural repertoire and a TRBV6 gene product from a natural repertoire.

BACKGROUND

T cell receptors (TCRs) mediate the recognition of specific major histocompatibility complex (MHC)-restricted peptide antigens by T cells and are essential to the functioning of the cellular arm of the immune system. In humans, MHC molecules are also known as human leukocyte antigens (HLA) and both terms are used synonymously herein. The terms 'peptide antigen' peptide-MHC' and 'peptide-HLA' refer to the antigen recognised by TCRs. TCRs exist only in membrane bound form and for this reason TCRs have historically been very difficult to isolate. Most TCRs are composed of two disulphide linked polypeptide chains, the alpha and beta chain.

TCRs are described herein using the International Immunogenetics (IMGT) TCR nomenclature and links to the IMGT public database of TCR sequences. Native alpha-beta heterodimeric TCRs have an alpha chain and a beta chain. Broadly, each chain comprises variable, joining and constant regions, and the beta chain also usually contains a short diversity region between the variable and joining regions, but this diversity region is often considered as part of the joining region. Each variable region comprises three hypervariable CDRs (Complementarity Determining Regions) embedded in a framework sequence; CDR3 is believed to be the main mediator of antigen recognition. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus "TRAV9" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5" defines a TCR Vβ region having unique framework and CDR1 and CDR2 sequences, but with only a partly defined CDR3 sequence. It is known that there are 54 alpha variable genes, of which 44 are functional, and 67 beta variable genes, of which 42 are functional, within the alpha and beta loci respectively (Scaviner D. and Lefranc M. P. (2000) Exp Clin Immunogenet, 17(2), 83-96; Folch G. and Lefranc M. P. (2000) Exp Clin Immunogenet, (2000) 17(1), 42-54; T cell Receptor Factsbook", (2001) LeFranc and LeFranc, Academic Press, ISBN 0-12-441352-8. As is known to those skilled in the art definitions of functionality may vary. Thus, for the sake of clarity, we consistently refer to the International Immunogenetics (IMGT) TCR nomenclature as found at the IMGT website imgt.org (as accessed 17 Aug. 2015).

The joining regions of the TCR are similarly defined by the unique IMGT TRAJ and TRBJ nomenclature, and the constant regions by the IMGT TRAC and TRBC nomenclature (Scaviner D. and Lefranc M. P. (2000) Exp Clin Immunogenet, 17(2), 97-106; Folch G. and Lefranc M. P. (2000) Exp Clin Immunogenet, 17(2), 107-14; T cell Receptor Factsbook", (2001) LeFranc and LeFranc, Academic Press, ISBN 0-12-441352-8).

The beta chain diversity region is referred to in IMGT nomenclature by the abbreviation TRBD, and, as mentioned, the concatenated TRBD/TRBJ regions are often considered together as the joining region.

The gene pools that encode the TCR alpha and beta chains are located on different chromosomes and contain separate V, (D), J and C gene segments, which are brought together by rearrangement during T cell development. This leads to a very high diversity of T cell alpha and beta chains due to the large number of potential recombination events that occur between the 54 TCR alpha variable genes and 61 alpha J genes or between the 67 beta variable genes, two beta D genes and 13 beta J genes. The recombination process is not precise and introduces further diversity within the CDR3 region. Each alpha and beta variable gene may also comprise allelic variants, designated in IMGT nomenclature as TRAVxx*01 and *02, or TRBVx-x*01 and *02 respectively, thus further increasing the amount of variation. In the same way, some of the TRBJ sequences have two known variations. (Note that the absence of a"*" qualifier means that only one allele is known for the relevant sequence). The natural repertoire of human TCRs resulting from recombination and thymic selection has been estimated to comprise approximately $10^6$ unique beta chain sequences, determined from CDR3 diversity (Arstila, T. P., et al (1999) Science, 286(5441), 958-61) and could be even higher (Robins, H. S. et al. (2009) Blood, 114(9), 4099-4107). Each beta chain is estimated to pair with at least 25 different alpha chains thus generating further diversity (Arstila, T. P., et al (1999) Science, 286(5441), 958-61).

In the present specification and claims, the term "TCR alpha (or α) variable domain" therefore refers to the concatenation of TRAV and TRAJ regions; a TRAV region only; or TRAV and a partial TRAJ region, and the term TCR alpha (or a) constant domain refers to the extracellular TRAC region, or to a C-terminal truncated or full length TRAC sequence. Likewise the term "TCR beta (or β) variable domain" may refer to the concatenation of TRBV and TRBD/TRBJ regions; to the TRBV and TRBD regions only; to the TRBV and TRBJ regions only; or to the TRBV and partial TRBD and/or TRBJ regions, and the term TCR beta (or β) constant domain refers to the extracellular TRBC region, or to a C-terminal truncated or full length TRBC sequence.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-

441352-8 also discloses sequences defined by the IMGT nomenclature, but because of its publication date and consequent time-lag, the information therein sometimes needs to be confirmed by reference to the IMGT database.

It has long been desirable to identify TCRs consisting essentially of natural alpha and beta chain sequences that specifically bind to particular antigens, such that for example the TCRs, or their soluble analogues, can be developed to provide basis for potential therapeutics. The antigens recognised by the identified TCRs may be associated with a disease, such as cancer, viral infections, inflammatory diseases, autoimmune diseases, parasitic infections and bacterial infections. Therefore, such therapies can be used for the treatment of said diseases.

Furthermore, once TCRs have been identified and their sequences determined, mutations can be introduced that result in an increase in affinity or half-life, as needed, such as described in WO2012/013913.

TCRs that are suitable for therapeutic use should possess various qualities, such as having the ability to fold correctly and stably, the ability to be manufactured efficiently and consistently, and to have low immunogenicity in order to be successful in a therapeutic setting. The most important and fundamental requirement is that TCRs for therapeutic use must exhibit a high degree of specificity to their target antigen. TCRs that bind to one or more, and in particular several, antigens presented by cells that are not the intended target of the TCR, pose an increased risk of toxicity when administered in vivo because of potential off target reactivity. Such highly cross-reactive TCRs are not suitable for therapeutic use.

Therefore there is a need for ways to identify specific TCRs suitable for therapeutic or diagnostic use, whilst at the same time avoiding the highly cross reactive TCRs that are not suitable for such applications.

Traditionally, attempts to identify TCRs that specifically bind to disease-associated antigens, such as cancer, viral, autoimmune, inflammatory, parasite or bacterial antigens, have been limited to the use of blood samples taken from volunteer donors. Such samples are used to isolate T cells and their corresponding TCRs which bind disease associated antigens. This approach generally requires at least 20 donors to have a reasonable expectation of success. The process is long and labour intensive, and there is no guarantee of identifying antigen binding TCRs. Where functional TCRs are identified, they often have weak affinity for antigen, low specificity, and/or do not fold properly in vitro. The diversity of T cells that are able to be screened is limited to the T cell diversity within donors. Some disease-associated antigens, including the majority of cancer-antigens, are self-antigens; since thymic selection serves to remove TCRs that recognise self-antigens, TCRs specific for disease associated antigens may not be present in the natural repertoire of the donors, or else may have weak affinity for antigen.

Attempts to design a library for the isolation of new TCRs with antigen binding specificity have been on-going for several years. TCR libraries are far more difficult to create than comparable antibody libraries, since TCR chains are less stable and often do not display correctly. The complexities involved in constructing a library of TCRs are enormous. Retaining variation in CDR3 length, (as found in natural repertoires) is preferable. A substantial portion of any library is generally lost to stop codons, frame shifts, folding problems and TCR chain combinations that could simply never bind to an HLA complex. Taking into account the huge number of variable alpha and variable beta genes, as well as the J and D genes, the chance of producing and identifying a functional folding alpha chain and a functional folding beta chain that together form a TCR that binds to an antigenic peptide with the required specificity, is extremely low.

A number of attempts at constructing libraries have been made. The first herein described below are based on synthetic TCR libraries; that is, the TCRs in the library contain mutations, typically within the CDRs, which have been introduced in vitro using random mutagenesis. Therefore, the sequences of any individual TCR chain contained in these libraries may not correspond to any found in a natural repertoire. The whole library will not correspond to a natural repertoire due to only certain mutations being present in the synthetic libraries. In the previously disclosed synthetic libraries random mutations were introduced into the CDR regions of alpha and beta chains of a single known TCR, such that all TCRs in the library contain the same alpha and beta framework sequence but with randomly generated CDR sequences. Further analysis of the library demonstrated that it was not successful for the identification of antigen specific TCRs. Specifically, it was found that a large proportion of the TCR chains were non-functional, for various reasons: in many cases the sequences were truncated or contained frameshifts. In other cases, although full length TCR chains were identified they were unable to fold correctly; finally, TCRs isolated from the library were not able to specifically bind an antigen when subjected to further testing. It is thought that the non-natural diversity in these synthetic libraries may be one reason why the libraries were not successful. The introduction of non-natural mutations may interfere with proper TCR function. Furthermore, the introduced diversity in CDR3 may be limited compared to a natural TCR repertoire. As exemplified by CDR3 sequence length in a natural repertoire, a huge diversity in CDR3 sequences is generated during TCR assembly in T cells. By basing a library on mutations at specific locations, the diversity of CDR3 sequences may be very much restricted, particularly in respect of the CDR3 sequence length. Finally, non-natural TCR sequences will not have been subjected to the thymic selection process that occurs in vivo.

These reasons go some way to explain, without wishing to be bound by theory, why the attempts to build libraries from which specifically binding TCRs were hoped to be identified, described below, were not successful.

WO2005/116646 describes a library based on a known (natural) TCR in which the six CDRs were mutated individually or in combination, i.e. all TCRs in the library were non-natural but based on a naturally identified TCR framework region. WO 2005/114215 further relates to products obtained from such a library. The library was screened with several other antigens (in addition to that to which the original TCR bound). However, this resulted in only one productive full-length TCR sequence being isolated. In further experiments, it was found that this TCR was cross reactive.

Thus, libraries based on in vitro-mutated TCRs have been constructed, but have not enabled the isolation of new TCRs with sufficient antigen binding specificity to be useful.

A library based on an entirely natural repertoire wherein the naturally derived alpha and beta chains were mixed randomly, (as discussed below), has been constructed but was not successful in identifying any TCRs which specifically bind antigen.

In particular, WO2005/116074 describes a library of nucleoproteins, each displaying on its surface a polypeptide comprising a native TCR alpha variable domain sequence or a native TCR beta variable domain sequence. The library described in this publication was constructed from a number of alpha and beta chains; 43 V alpha class genes and 37 V beta class genes were amplified from the mRNA pool used to generate the library. It is stated in this document that three rounds of phage display led to the isolation of clones which bound to the peptide being tested. These clones are described as having been identified during ELISA screening as determined by strong ELISA signals. However, strong ELISA signals were also observed when these clones were tested for binding an alternative peptide-HLA; therefore, the TCR clones were not specific for peptide. Further analysis of this library indicated similar issues to those described above for synthetic libraries in that they contained a large proportion of non-productive TCR chains as well as TCRs that were unable to fold correctly. The library described therein was thus not useful for identifying new antigen-binding TCRs.

Therefore, there is need for a TCR library that enables the more reliable identification of functional, antigen-specific TCRs comprising an alpha chain variable domain and a beta chain variable domain, which library may be screened using a variety of peptide antigens in order to identify such useful TCRs. The identified TCRs can then either be used at their natural affinity or could be used in, for example, phage display maturation, to enhance affinity.

The inventors have found that certain beta chains can, when present in a TCR library of the invention, form TCRs that often exhibit high levels of cross reactivity. The inventors have found that when a library containing such beta chains is panned for TCRs specific for a desired antigen using standard methods, such cross reactive TCRs appear to "dominate" the outputs of any library containing such beta chains, meaning that specific TCRs are more difficult or even impossible to identify.

SUMMARY OF INVENTION

The present invention provides in a first aspect a library of particles displaying a plurality of T cell receptors (TCRs), wherein the plurality of TCRs: i) consists essentially of TCRs comprising an alpha chain comprising an alpha chain variable domain and beta chain comprising a beta chain variable domain that does not comprise one or more of a TRBV5-1, 5-3, 5-4, 5-5, 5-6, 5-7 or 5-8 gene product; ii) comprises more than one TRAV gene product and/or more than one TRBV gene product; and iii) does not consist essentially of TCRs comprising a TRAV12-2 gene product from a natural repertoire and a TRBV6 gene product from a natural repertoire and TCRs comprising a TRAV21 gene product from a natural repertoire and a TRBV6 gene product from a natural repertoire. Variable domains are as described above i.e. they may also comprise complete or partial TRAJ or TRBD and/or TRBJ regions, respectively.

The beta chain variable domain may also not comprise a TRBV10-2 gene product and/or 10-3 gene product. The beta chain variable domain may also not comprise a TRBV2 gene product and/or a TRBV9 gene product and/or a TRBV14 gene product. The beta chain variable domain may not comprise any TRBV5 gene product. Alternatively, the beta chain variable domain may comprise a TRBV5-1 gene product.

The CDR3 sequence of the alpha and/or beta variable domains may be obtained from a natural repertoire. Alternatively the CDR3 sequence of the alpha and/or beta variable domains may be designed artificially and may contain one or more non-natural mutations. The framework, CDR1 and/or CDR2 sequences of the variable domains may contain a non-natural mutation.

The alpha chain variable domain and the beta chain variable domain may be displayed as a single polypeptide chain, or as separate dimerised polypeptide chains.

The TCRs are displayed on particles and may comprise a non-native disulphide bond between a constant region of the alpha chain and a constant region of the beta chain. Such non-native di-sulphide bonds are described for example, in WO 03/020763. Alternatively, the TCRs displayed on particles may comprise a native disulphide bond between a constant region of the alpha chain and a constant region of the beta chain.

Each alpha chain and each beta chain may comprise a dimerization domain, which is preferably heterologous. Such a heterologous domain may be a leucine zipper, a 5H3 domain or hydrophobic proline rich counter domains, or other similar modalities, as known in the art.

The particles forming the library may be phage particles. Alternatively, the library may be a library of ribosomes. Alternatively, the library may be a yeast display library, so the particles may be yeast cells. The particles may be mammalian cells.

The library may be suitable for screening with a peptide antigen. Such a peptide antigen may comprise HLA, such as HLA-A, such as HLA-A2 or A3.

A further aspect of the invention provides an isolated T cell receptor (TCR) comprising a TCR alpha chain variable domain and a TCR beta chain variable domain obtained from a library of the first aspect of the invention. The TCR may be soluble, or may be suitable for expression on cells. Also encompassed by the invention is a nucleic acid encoding a TCR alpha chain variable domain and/or a beta chain variable domain of the said TCR.

As a further aspect, the invention provides the use of a library of the first aspect, to identify a TCR that specifically binds to a peptide antigen. The peptide antigen may be used to screen the library of the invention for a TCR to which it binds. The peptide antigen may comprise HLA, such as HLA-A, B, C, G or E, or non-classical HLAs such as CD1. The peptide antigen may comprise HLA-A2 or A3.

A further aspect provides a method of obtaining a TCR that specifically binds a peptide antigen, comprising screening the library of the first aspect with the peptide antigen, the method comprising; a) panning the library using as a target the peptide antigen; b) repeating step a) one or more times; c) screening the phage clones identified in steps a) or b); and d) identifying a TCR that specifically binds the peptide antigen. The peptide antigen may comprise HLA, such as HLA-A, B, C, G or E, or non-classical HLAs such as CD1. The peptide antigen may comprise HLA-A2 or A3.

In a further aspect, the invention is concerned with a method of making a library of particles, the library displaying a plurality of different TCRs, the method comprising: i) obtaining a plurality of nucleic acids that encode different TRAV alpha chain variable domains; ii) obtaining a plurality of nucleic acids that encode different TRBV beta chain variable domains, wherein the plurality of nucleic acids does not comprise nucleic acids that encode at least one of TRBV5-1, 5-3, 5-4, 5-5, 5-6, 5-7 or 5-8 beta chain variable domains; iii) cloning the TRAV alpha chain variable domain encoding nucleic acids into expression vectors; iv) cloning the TRBV beta chain variable domain encoding nucleic acids into the same or different vectors; and v) expressing the vectors in particles, thereby generating a library consisting essentially of TCRs comprising an alpha chain variable domain and a beta chain variable domain encoded by the nucleic acids.

A further aspect concerns a method of making a library of particles, the library displaying a plurality of different TCRs, the method comprising: i) obtaining a plurality of nucleic acids that encode different TRAV alpha chain variable domains using primers that hybridise to nucleic acids encoding TRAV alpha chain variable domains; ii) obtaining a plurality of nucleic acids that encode different TRBV beta chain variable domains using primers that hybridise to nucleic acids encoding TRBV beta chain variable domains, wherein the primers that hybridise to one or more nucleic acids encoding TRBV do not comprise primers that hybridise to nucleic acids that encode at least one of a TRBV5-1, 5-3, 5-4, 5-5, 5-6, 5-7 or 5-8 beta chain variable domains; iii) cloning the TRAV alpha chain variable domain encoding nucleic acids into expression vectors; iv) cloning the TRBV beta chain variable domain encoding nucleic acids into the same or different vectors; and v) expressing the vectors in particles, thereby generating a library consisting essentially of TCRs comprising an alpha chain variable domain and a beta chain variable domain encoded by the nucleic acids to which said primers hybridise.

A forward primer may be designed to hybridise to a TRAV locus or a TRBV locus. A reverse primer may be designed to hybridise, at least in part to the alpha or beta constant region, respectively, such that the resulting PCR product contains the variable regions, through to the joining regions and at least part of the constant region. Transcription, translation or post-translation events may result in truncation, or deletion of some or all of the joining and/or constant regions, including the diversity region in the case of the beta chain sequences.

The primers that hybridise to nucleic acids encoding TRBV beta chain variable domains, may also exclude primers that hybridise to nucleic acids encoding TRBV10-2 and/or TRBV10-3 gene products. The primers may also exclude primers that hybridise to nucleic acids encoding TRBV2 and/or TRBV9 and/or TRBV14 gene products.

The primers that hybridise to nucleic acids encoding TRBV beta chain variable domains, may exclude primers that hybridise to nucleic acids encoding any TRBV5 gene product. Alternatively, the primers may include primers that hybridise to nucleic acids encoding a TRBV5-1 gene product.

All or part of each of the nucleic acids of the plurality of nucleic acids in step (i) and/or step (ii) encoding a TRAV gene product or a TRBV gene product may be obtained synthetically and/or may be designed artificially.

All or part of the framework region, CDR1, CDR2 and/or CDR3 may be obtained synthetically and/or designed artificially. At least the CDR3 sequence of the nucleic acids of step (i) and step (ii) may be designed artificially, or may be from a natural repertoire.

The nucleic acid sequences of step (i) and step (ii) may be obtained from a natural repertoire, or may be partially or completely designed artificially.

In some instances, non-natural mutations may be introduced to the nucleic acid sequences prior to step iii). The mutations may be introduced after step i) and/or ii), or after steps iii) and/or iv).

In either method of making a library of the invention the TCR alpha chain variable domain and the TCR beta chain variable domain are preferably expressed from the same vector, i.e. nucleic acids that encode each of the alpha and beta chain variable domains are cloned into the same vector.

The alpha chain variable domain and the beta chain variable domain may be expressed as a single polypeptide or they may be expressed as separate polypeptides.

The invention provides as a further aspect a method of obtaining a T cell receptor that specifically binds a peptide antigen, comprising screening a library of the first or second aspect of the invention with the peptide antigen. The peptide antigen may comprise HLA, such as HLA-A, B, C, G or E, or non-classical HLAs such as CD1. The peptide antigen may comprise HLA-A2 or A3.

A particle displaying on its surface a TCR in accordance with the invention is also included in the scope of the present invention.

The library of the invention is non-naturally occurring as it includes TCR(s) that are not naturally occurring or those that would be considered "isolated" as that term is used herein; and accordingly, TCRs of the invention are likewise patent-eligible subject matter as such TCRs are not naturally occurring or those that would be considered "isolated" as that term is used herein. Similarly, cells and particles of the invention are patent-eligible subject matter because by displaying on its surface or expressing a TCR of the invention, the cell or particle is not naturally occurring or that which would be considered "isolated" as that term is used herein.

It is also noted that in this disclosure and particularly in the claims and/or paragraphs, terms such as "comprises", "comprised", "comprising" and the like can have the usual meaning attributed to it; e.g., they can mean "includes", "included", "including", and the like; and that terms such as "consisting essentially of" and "consists essentially of" have the meaning generally ascribed to them e.g., they allow for elements not explicitly recited, but exclude elements that are found in the prior art or that affect a basic or novel characteristic of the invention.

These and other embodiments are disclosed or are obvious from and encompassed by, the following description.

BRIEF DESCRIPTION OF THE DRAWINGS

The following detailed description, given by way of example, but not intended to limit the invention solely to the specific embodiments described, may best be understood in conjunction with the accompanying drawings, wherein:

FIG. 2 details the general primer sequences used in the library construction;

FIG. 3 details the TRAV specific primers used in library construction;

FIG. 4 details the TRBV specific primers used in library construction;

FIG. 5 shows A) initial ELISA screening results from panning the library of Example 5 with two different peptide-HLA complexes and B) further specificity testing of TCRs from positive ELISA clones;

FIG. 6 shows A) initial ELISA screening results from panning the comparative library of Example 5 with two different peptide-HLA complexes and B) further specificity testing of TCRs from positive ELISA clones;

FIG. 7 shows A) Initial ELISA screening results from panning the library of Example 6 with two different peptide-HLA complexes and B) further specificity testing of TCRs from positive ELISA clones;

FIG. 8 shows A) Initial ELISA screening results from panning the library of Example 7 one peptide-HLA complexes and B) further specificity testing of TCRs from positive ELISA clones;

FIG. 9 shows A) Initial ELISA screening results from panning the library of Example 8 with one different peptide-HLA complexes and B) further specificity testing of TCRs from positive ELISA clones;

FIG. 10 shows A) Initial ELISA screening results from panning the library of Example 9 with one peptide-HLA complexes and B) further specificity testing of a TCR from a positive ELISA clone;

FIG. 11 shows A) Initial ELISA screening results from panning the library of Example 10 with two different peptide-HLA complexes and B) further specificity testing of TCRs from positive ELISA clones;

FIG. 12 shows A) Initial ELISA screening results from panning the comparative library of Example 10 with two different peptide-HLA complexes and B) further specificity testing of TCRs from positive ELISA clones;

DETAILED DESCRIPTION OF THE INVENTION

Figure 1:
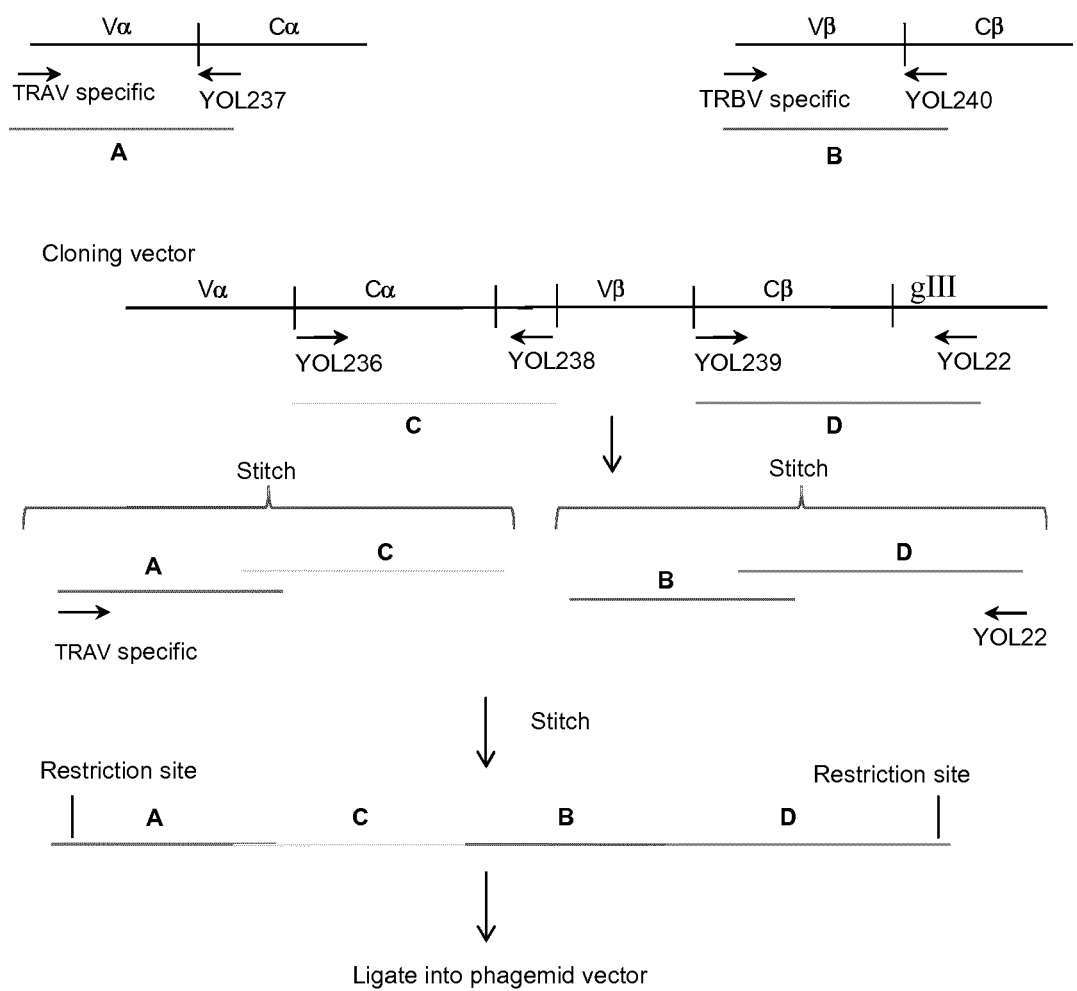
FIG. 1 outlines the cloning strategy used for library creation.

A library of particles displaying a plurality of T cell receptors (TCRs), wherein the plurality of TCRs: i) consists essentially of TCRs comprising an alpha chain comprising an alpha chain variable domain and beta chain comprising a beta chain variable domain that does not comprise one or more of a TRBV5-1, 5-3, 5-4, 5-5, 5-6, 5-7 or 5-8 gene product; ii) comprises more than one TRAV gene product and/or more than one TRBV gene product; and iii) does not consist essentially of TCRs comprising a TRAV12-2 gene product from a natural repertoire and a TRBV6 gene product from a natural repertoire and of TCRs comprising a TRAV21 gene product from a natural repertoire and a TRBV6 gene product from a natural repertoire.

Such a TRBV6 gene product may be one or more of a 6-1, 6-2, 6-3, 6-5, 6-6 gene product.

A TRBV5 gene may actually designate one or all of the genes TRBV5-1, 5-3, 5-4, 5-5, 5-6, 5-7 or 5-8.

The library of the present invention does not therefore include (i.e. the TCRs of the library do not comprise) at least one of these gene products. For example, the library may comprise TRBV5-3, 5-4, 5-5, 5-6, 5-7 and 5-8 but not 5-1. Alternatively, the library may comprise, for example, 5-1, 5-6 and 5-8 i.e. does not comprise 5-3, 5-5, 5-4 and 5-7. The library may comprise all TRBV5 gene products apart from TRBV5-4 and TRBV5-5. In particular, the library may not comprise a TBRV5-5 and/or a TRBV5-6 gene product.

The library may not comprise any TRBV5 gene product, meaning that each of TRBV5-1, 5-3, 5-4, 5-5, 5-6, 5-7 and 5-8 are not represented or present in the library, i.e. all of TRBV5-1, 5-3, etc. are absent.

The library may include TCRs that comprise a TRBV5-1 gene product, but not TCRS that comprise any of TRBV5-3, 5-4, 5-5, 5-6, 5-7 or 5-8.

The library may not comprise a TRBV10-2 or TRBV10-3 gene product in addition to not comprising one or more or all of the TRBV5 gene products i.e. the library may exclude a TRBV5 gene product and exclude a TRBV10-2 and/or TRBV10-3 gene product.

The library may not comprise a TRBV2, and/or a TRBV9 and/or a TRBV14 gene product. The library may comprise- TRBV2 and not TRBV9 or TRBV14. The library may comprise TRBV14 and not TRBV9 or TRBV2. The library may comprise TRBV9 and not TRBV14 or TRBV2.

The library may not comprise a TRBV5 gene product, and may not comprise TRBV10-2 and 10-3 gene products. The TCRs of such a library may comprise separate α and β chains e.g. a heterodimer of a TRAV gene product and a TRBV gene product that is not a TRBV5, a TRBV10-2 or a TRBV10-3 gene product. The TCRs of the library may be displayed as a single polypeptide chain comprising a TRAV gene product and a TRBV gene product that is not a TRBV5-1, 5-3, 5-4, 5-5, 5-6, 5-7, 5-8, 10-2 or 10-3 gene product.

The library may not comprise a TRBV5-3, 5-4, 5-5, 5-6, 5-7 or 5-8 gene product, and may not comprise a TRBV10-2, TRBV10-3, TRBV2, TRBV9 and a TRBV14 gene product. Such a library may comprise TCRs that are displayed as a single polypeptide chain comprising a TRAV gene product and a TRBV gene product that is not TRBV5-3, 5-4, 5-5, 5-6, 5-7, 5-8, 10-2, 10-3, 2, 9 or 14 gene product. The TCRs of such a library may comprise separate a and β chains e.g. a heterodimer of a TRAV gene product and a TRBV gene product that is not a TRBV5-3, 5-4, 5-5, 5-6, 5-7, 5-8, 10-2, 10-3, 2, 9 or 14 gene product.

The library may comprise multiple TRAV gene products, and multiple TRBV gene products. Such a library may comprise TCRs that consist of a separate TRAV gene product and a separate TRBV gene product that form a heterodimer or TCRs that are displayed as a single chain polypeptide. A library may comprise TCRs comprising gene products of any number of TRAV genes and TRBV genes, provided that one or more TRAV and/or one or more TRBV gene products are present. A library may comprise TCRs comprising gene products of 1, 5, 10, 15, 20, 25, 30, 35 TRAV genes and gene products of 1, 5, 10, 15, 20, 25, 30, 35 TRBV genes.

The library may comprise a single TRAV gene product, and multiple TRBV gene products. The library may comprise TCRs that consist of a separate TRAV gene product and a separate TRBV gene product that form a heterodimer or a TRAV gene product and a TRBV gene product that are displayed as a single polypeptide chain.

The library may comprise multiple TRAV gene products, and a single TRBV gene product. The library may comprise TCRs that consist of a separate TRAV gene product and a separate TRBV gene product that form a heterodimer or a TRAV gene product and a TRBV gene product that are displayed as a single polypeptide chain.

By "consisting essentially of" it is meant that the majority of the TCRs in the library do not, for example, comprise a TRBV 5-1, 5-3, 5-4, 5-5, 5-6, 5-7 and 5-8 gene product but that the minority may comprise such a gene product due to, for example, non-specific hybridisation of primers when making the library, or regions of high homology between genes in the beta variable loci genes. The amount of the majority may be defined as below. Alternatively, a TRBV5-1 gene product may be present.

The plurality of TCRs may consist of 90% of TCRs comprising an alpha chain variable domain comprising a TRAV gene product and a beta chain variable domain comprising a TRBV gene product. The plurality of TCRs may consist of 95%, 96%, 97%, 98%, 99%, 100% of TCRs that do not comprise a beta chain variable domain comprising a TRBV5-1, 5-3, 5-4, 5-5, 5-6, 5-7 or 5-8 gene product. The plurality of TCRs may consist of 95%, 96%, 97%, 98%, 99%, 100% of TCRs that do not comprise any TRBV5 gene product. The plurality of TCRs may consist of 95%, 96%, 97%, 98%, 99%, 100% of TCRs that do also not comprise a TRBV10-2 or TRBV10-3 and/or a TRBV2, and/or a TRBV9 and/or a TRBV14 gene product. A TRBV5-1 gene product may be present in more than 5% of TCRs of the library.

The remaining 10% or less of the plurality of TCRs may comprise a TRBV5-1, 5-3, 5-4, 5-5, 5-6, 5-7 or 5-8 gene product. The remaining 10% or less of the plurality of TCRs may comprise a TRBV5 gene product and/or a TRBV10-2 or TRBV10-3 gene product, and/or a TRBV2, TRBV9 or TRBV14 gene product.

The proportion of TCRs comprising at least one of a TRBV5-1, 5-3, 5-4, 5-5, 5-6, 5-7 or 5-8 gene product may be 10%, 9%, 8%, 7%, 6%, 5%, 4%, 3%, 2%, 1%, 0.5%, 0.2%, 0.2%, less than 0.1% or 0%. The proportion of TCRs comprising any TRBV5 gene product (or alternatively any of TRBV5-3, 5-4, 5-5, 5-6, 5-7 and 5-8) may be 10%, 9%, 8%, 7%, 6%, 5%, 4%, 3%, 2%, 1%, 0.5%, 0.2%, 0.2%, less than 0.1% or 0%. The proportion of TCRs comprising any TRBV5 gene product (alternatively excluding TRBV5-1) or any TRBV10-2 or TRBV10-3 and/or TRBV2, TRBV9, TRBV14 gene product may be in total 10%, 9%, 8%, 7%, 6%, 5%, 4%, 3%, 2%, 1%, 0.5%, 0.2%, 0.2%, less than 0.1% or 0%.

The library of the present invention may therefore contain a plurality of TCRs each having the following alpha chain and beta chain V, J, (D) and C gene usage:

alpha chain—TRAVyy/TRAJxx/TRAC; and beta chain—TRBVzz/TRBDx/TRBJxx/TRBC1, TRBC2 or a chimera of C1 and C2, wherein yy is any of the alpha V genes, xx is any of the 61 alpha J genes or 13 beta J genes, respectively, zz is any of the TRBV beta genes apart from one or more of TRBV5-1, 5-3, 5-4, 5-5, 5-6, 5-7 or 5-8, and Dx represents either of the 2 beta D genes. Alternatively, TRBV5-1 may be represented by zz.

Alternatively zz may represent any TRBV5 gene or zz may represent none of the TRBV5 genes.

zz may not represent any TRBV5 gene, and/or TRBV10-2, TRBV10-3, TRBV2, TRBV9 and TRBV14. TRBV5-1 may be represented by zz.

As discussed above the J, D or C regions may each be fully or partially present or absent.

Preferably the V, D, J and C genes are human. Preferably the V genes are functional.

By gene product it is also meant a polypeptide, which may include post-translation modification, that is encoded by the nucleic acid sequence of the indicated gene. As is known to the skilled person, each TCR alpha or beta chain variable domain gene contains variation in the CDR3 regions, as discussed above, meaning that the gene products will also vary enormously.

The library comprises more than one (i.e. at least two) of the following gene products, in accordance with the invention.

| IMGT gene name<br>Scaviner et al 2000 (Exp Clin Immunogenet 17: 83-96) |
| --- |
| TRAV41 |
| TRAV40 |
| TRAV39 |
| TRAV38-2/DV8 |
| TRAV38-1 |
| TRAV37 |
| TRAV36/DV7 |
| TRAV35 |
| TRAV34 |
| TRAV26-2 |
| TRAV33 |
| TRAV32 |
| TRAV31 |
| TRAV30 |
| TRAV29/DV5 |
| TRAV28 |
| TRAV27 |
| TRAV8-7 |
| TRAV26-1 |
| TRAV25 |
| TRAV24 |
| TRAV23/DV6 |
| TRAV22 |
| TRAV21 |
| TRAV20 |
| TRAV19 |
| TRAV18 |
| TRAV17 |
| TRAV16 |
| TRAV8-6 |
| TRAV12-3 |
| TRAV15 |
| TRAV9-2 |
| TRAV14/DV4 |
| TRAV13-2 |
| TRAV8-5 |
| TRAV8-4 |
| TRAV12-2 |
| TRAV13-1 |
| TRAV8-3 |
| TRAV8-2 |
| TRAV12-1 |
| TRAV11 |
| TRAV10 |
| TRAV9-1 |
| TRAV8-1 |
| TRAV7 |
| TRAV6 |
| TRAV5 |
| TRAV4 |
| TRAV3 |
| TRAV2 |
| TRAV1-2 |
| TRAV1-1 |

| Folch et al 2000 (Exp Clin Immunogenet 17: 42-54, table 2 |
| --- |
| TRBV1 |
| TRBV2 |
| TRBV3-1 |
| TRBV3-2 |
| TRBV4-1 |
| TRBV4-2 |
| TRBV4-3 |
| TRBV5-1 |
| TRBV5-2 |
| TRBV5-3 |
| TRBV5-4 |
| TRBV5-5 |
| TRBV5-6 |
| TRBV5-7 |
| TRBV5-8 |
| TRBV6-1 |
| TRBV6-2 |
| TRBV6-3 |
| TRBV6-4 |
| TRBV6-5 |
| TRBV6-6 |
| TRBV6-7 |
| TRBV6-8 |
| TRBV6-9 |
| TRBV7-1 |
| TRBV7-2 |
| TRBV7-3 |
| TRBV7-4 |

-continued

Folch et al 2000 (Exp Clin Immunogenet 17: 42-54, table 2)

TRBV7-5
TRBV7-6
TRBV7-7
TRBV7-8
TRBV7-9
TRBV8-1
TRBV8-2
TRBV9
TRBV10-1
TRBV10-2
TRBV10-3
TRBV11-1
TRBV11-2
TRBV11-3
TRBV12-1
TRBV12-2
TRBV12-3
TRBV12-4
TRBV12-5
TRBV13
TRBV14
TRBV15
TRBV16
TRBV17
TRBV18
TRBV19
TRBV20-1
TRBV21-1
TRBV22
TRBV23-1
TRBV24-1
TRBV25-1
TRBV26
TRBV27
TRBV28
TRBV29-1
TRBV30

The alpha and/or beta chain sequences may be obtained from a natural repertoire. By "from a natural repertoire" it is meant that at least the CDR3 sequences within the plurality of TCRs corresponds directly to those of a natural repertoire, with respect to, for example, sequence length and amino acid composition. In this case the alpha and beta chain variable domains may be expressed from DNA sequences that have been amplified from human donors. In other words, the diversity of the alpha and/or beta CDR3 domains of the TCRs of the library has been naturally generated during T cells development in vivo. Furthermore, this means that the sequences of all the alpha and beta chains in the library will have been selected for during thymic selection. The random combination of these alpha and beta chains, which occurs during library creation, may result in an alternative repertoire of alpha beta chain combinations compared to that originally present in vivo (i.e. in the donor(s)). The DNA sequences may be obtained indirectly e.g. by producing cDNA from donor mRNA.

The cDNA sequences may then be used as templates to produce DNA sequences from which the plurality of different TCRs is produced.

Alternatively, the alpha and/or beta chain sequences may be designed artificially. By "designed artificially" it is meant that the diversity of CDR3 sequences within the plurality of TCRs may not correspond to a natural repertoire. In this case the sequences may be generated, for example, using DNA synthesis with degenerate oligonucleotides, such as NNK, NNN, or NNS, incorporated at defined locations within the CDR3 sequence, or through the introduction of non-natural mutations as defined below. Preferably, the diversity of artificial designed CDR3 sequences in the library is designed to resemble that of a natural repertoire, with respect to, for example, variation in sequence length and amino acid composition. Preferably the total diversity of designed artificially CDR3 sequences within the library is greater than that obtained from a natural repertoire.

Therefore, by designed artificially it is meant that the sequence has the same or similar (i.e. 90% sequence identity to an amino acid sequence to a TRAV or TRBV gene product from a natural repertoire. The sequence may not be 100% identical to the sequence of any TRAV or TRBV gene product as found in a natural repertoire. The sequence may have been, for example and as known to the skilled person, optimised for codon usage, folding ability, stability, removal of cleavage sites, removal/addition of glycosylation or amidation or other post translation modification sites. Such modification may be amino acid substitution, addition or deletion, i.e. by introducing one or more non-natural mutations, which is encompassed within the definition of "designed artificially". The substitution may be a conservative amino acid substitution or a non-conservative amino acid substitution, as understood by the person skilled in the art. Typically, such modifications occur within the framework region of the TRAV and/or TRBV gene product.

Non-natural mutations may be introduced by any way known in the art. Non-natural mutations may be randomly generated, or specifically defined, or both. For example, randomly generated mutations may be incorporated at defined positions using site-saturation mutagenesis in which the native amino acid coding sequence is replaced by the coding sequence of all other naturally occurring amino acids; thereby, creating additional library diversity at a defined position. The method may involve replicating the DNA of interest using PCR amplification with degenerate synthetic oligonucleotides as primers. Preferably, such mutations are made within the CDR regions of the alpha and/or beta chain variable domain. Alternatively, or additionally, defined mutations, including insertions and deletions, may be introduced at certain positions using, for example, commercially available kits, such as the Quik Change Site Directed Mutagensis Kit from Stratagene.

The library may display TCRs where 10%, 15%, 20%, 25%, 30%, 40%, 50%, 60%, 70%, 75%, 80%, 85%, 90%, 95% or 100% of the alpha chain variable domains or beta chain variable domains comprise a non-natural mutation.

The library of the present invention preferably comprises at least $1 \times 10^8$ particles that display an αβ TCR chain combination.

The library may be a library of phage particles. Phage display is described in WO2004/044004.

Alternatively, the library is a library of ribosomes. Ribosome display is known in the art. The particles may be complete ribosomal complexes or parts thereof.

Yeast display systems may be used, meaning that the library may be a library of yeast cells.

An additional display methodology suitable for the creation of TCRs libraries is mammalian cell display. This system uses a retroviral vector to introduce the TCR alpha and beta chains into a TCR-negative T cell hybridoma. The method is further described in Chervin et al. (2008) J Immunol Methods, 339, 175-84; and Kessels et al. (2000) Proc Natl Acad Sci USA, 97, 14578-83).

Any library of particles that is able to display heterodimeric or single chain TCRs, as described, is encompassed by the invention.

Single chain TCRs include αβ TCR polypeptides of the type: Vα-L-Vβ, Vβ-L-Vα, Vα-Cα-L-Vβ, Vα-L-Vβ-Cβ or Vα-Cα-L-Vβ-Cβ, optionally in the reverse orientation, wherein Vα and Vβ are TCR α and β variable regions respectively, Cα and Cβ are TCR α and β constant regions respectively, and L is a linker sequence. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

The alpha and/or beta chain constant domain may be truncated relative to the native/naturally occurring TRAC/TRBC sequences. In addition, where present, the TRAC/TRBC may contain modifications. The alpha chain extracellular sequence may include a modification in relation to the native/naturally occurring TRAC whereby amino acid T48 of TRAC, with reference to IMGT numbering, is replaced with C48. Likewise, the beta chain extracellular sequence may include a modification in relation to the native/naturally occurring TRBC1 or TRBC2 whereby S57 of TRBC1 or TRBC2, with reference to IMGT numbering, is replaced with C57, and C75 is replaced by A75 and N89 replaced D89. These cysteine substitutions relative to the native alpha and beta chain extracellular sequences enable the formation of a non-native interchain disulphide bond which stabilises the refolded soluble TCR, i.e. the TCR formed by refolding extracellular alpha and beta chains. This non-native disulphide bond facilitates the display of correctly folded TCRs on phage, (Li, Y., et al. Nat Biotechnol 2005: 23(3), 349-54). In addition the use of the stable disulphide linked soluble TCR enables more convenient assessment of binding affinity and binding half-life. Alternative substitutions are described in WO03/020763. Alternatively, the alpha and beta constant domains may be linked by a disulphide bond which corresponds to that found in nature.

To further, or alternatively, stabilise the heterodimeric TCRs, each alpha chain and each beta chain may comprise a dimerization domain, which may be heterologous to the native TCR chain sequence.

In particular, the dimerization domain may be a leucine zipper. This term describes pairs of helical peptides which interact with each other in a specific fashion to form a heterodimer. The interaction occurs because there are complementary hydrophobic residues along one side of each zipper peptide. The nature of the peptides is such that the formation of heterodimers is very much more favourable than the formation of homodimers of the helices. Leucine zippers may be synthetic or naturally occurring, such as those described in WO99/60120. Alternative dimerization domains include disulphide bridge-forming elements. Alternatively, it may be provided by the SH3 domains and hydrophobic/proline rich counterdomains, which are responsible for the protein-protein interactions seen among proteins involved in signal transduction (reviewed by Schlessinger, (Schlessinger, J., Curr Opin Genet Dev. 1994 February; 4(1):25-30). Other natural protein-protein interactions found among proteins participating in signal transduction cascades rely on associations between post-translationally modified amino acids and protein modules that specifically recognise such modified residues. Such post-translationally modified amino acids and protein modules may form the dimerisation domain of the TCR chains of the library in accordance with the invention.

Without being bound by theory, the inventors believe that the presence of certain TRBV genes in a library prevent or hinder the routine identification of useful TCRs (for example those with suitable specificity) from said library. It is thought that certain TRBV chains encode for highly cross reactive TCRs, which, due to a selection pressure imparted by the panning procedure, results in the cross-reactive TCRs dominating the libraries that contain them. This can prevent specific, and therefore therapeutically useful, TCRs from being identified. The inventors have found that libraries which exclude the TRBV chains identified herein can be used for the identification of useful TCRs with a high degree of specificity for target antigen.

As a further aspect, the invention provides an isolated T cell receptor (TCR) comprising a TCR alpha chain variable domain and a TCR beta chain variable domain that does not comprise one of TRBV5-1, 5-3, 5-4, 5-5, 5-6, 5-7 or 5-8 gene products isolated from a library according to the first aspect of the invention. The TCR may not comprise any TRBV5 gene product. The TCR may not comprise a TRBV5 or TRBV10-2 or TRBV10-3 or a TRBV2, TRBV9 or a TRBV14 gene product. The TCR may comprise a TRBV5-1 gene product.

By isolated it is meant that the TCR is removed from its natural environment, i.e. not a TCR that is displayed naturally on a T cell in vivo.

The TCR may specifically bind to a peptide antigen. Such a TCR obtained from the library of the invention may bind with strong affinity and high specificity to the peptide antigen, as determined by, for example but not limited to, ELISA or BiaCore. The TCR may be taken through further affinity maturation such that binding affinity and/or half-life is increased. The TCR may be soluble, i.e. it may be cleaved from the transmembrane domain, such as described in WO 03/020763. The TCR may contain a non-native disulphide bond as described above. The TCR may be fused to detectable labels including, but not limited to, fluorescent labels, radiolabels, enzymes, nucleic acid probes and contrast reagents, or to therapeutic agents including, but not limited to, immunomodulators, radioactive compounds, enzymes (perforin for example) or chemotherapeutic agents (cisplatin for example) (WO2010/133828). The TCR may be non-naturally expressed on the surface of cells, preferably mammalian cells, more preferably immune cells, even more preferably T cells.

Binding affinity (inversely proportional to the equilibrium constant $K_D$) and binding half-life (expressed as T½) can be determined by any appropriate method. It will be appreciated that doubling the affinity of a TCR results in halving the $K_D$. T½ is calculated as In2 divided by the off-rate ($k_{off}$). So doubling of T ½ results in a halving in $k_{off}$. $K_D$ and $k_{off}$ values for TCRs are usually measured for soluble forms of the TCR, i.e. those forms which are truncated to remove hydrophobic transmembrane domain residues. Therefore it is to be understood that a given TCR meets the requirement that it has a binding affinity for, and/or a binding half-life for a peptide antigen if a soluble form of that TCR meets that requirement. Preferably the binding affinity or binding half-life of a given TCR is measured several times, at a defined temperature using the same assay protocol and an average of the results is taken. More preferable the binding affinity or binding half life is measured by surface plasmon resonance at a temperature of 25° C. A preferred method is given in Example 12.

For the purposes of the present invention, as described above, a TCR is a moiety having at least one TCR alpha and at least one TCR beta variable domain. Generally it will comprise both a TCR alpha variable domain and a TCR beta variable domain. They may be αβ heterodimers or may be single chain format, by which it is meant a single polypeptide contains both the alpha chain and the beta chain, such as described in WO 2004/033685. Single chain TCRs encompass αβ TCR polypeptides of the type: Vα-L-Vβ, Vβ-L-Vα, Vα-Cα-L-Vβ, Vα-L-Vβ-Cβ or Vα-Cα-L-Vβ-Cβ, optionally in the reverse orientation, wherein Vα and Vβ are TCR α and β variable regions respectively, Cα and Cβ are TCR α and β constant regions respectively, and L is a linker sequence. Alternatively the TCR may comprise a TCR α chain extracellular domain dimerised to a TCRβ chain extracellular domain by means of a pair of C-terminal dimerisation peptides, such as leucine zippers, such TCRs are described in WO 99/60120. For use in adoptive therapy, an αβ heterodimeric TCR may, for example, be transfected into cells, such as T cells, as full length chains having both cytoplasmic and transmembrane domains. If desired, an introduced disulphide bond between residues of the respective constant domains may be present (see for example WO 2006/000830). Alternatively, the alpha and beta constant domains may be linked by a disulphide bond which corresponds to that found in nature.

Included in the invention is a nucleic acid that encodes a TCR alpha chain variable domain and/or a TCR beta chain variable domain of the TCR of the invention. The alpha and beta chains may be expressed from separate nucleic acids or from one nucleic acid molecule. If from the same nucleic acid molecule, the alpha and beta chains may be expressed as independent polypeptides, or as a single chain.

The nucleic acid comprises a TRAV sequence and/or a TRBV nucleic acid sequence but does not comprise one of TRBV5-1, 5-3, 5-4, 5-5, 5-6, 5-7 or 5-8 nucleic acid sequence. The nucleic acid may also comprise a TRAJ sequence and/or a TRBD/TRBJ sequence. The nucleic acid may also comprise the TRAC and/or TRBC1 or TRBC2 nucleic acid sequence, or partial sequences thereof.

The nucleic acid may not comprise any TRBV5 sequence or a TRBV10-2 or a TRBV10-3 or a TRBV2, or a TRBV9 or TRBV14 sequence. The nucleic acid may, alternatively, comprise a TRBV5-1 sequence.

In a further aspect of the invention, the use of the library of the first aspect to identify a TCR that specifically binds a peptide antigen is provided. As mentioned, TCRs that bind specifically to a peptide antigen are desirable for a variety of reasons.

A further aspect of the invention provides a method of making a library of particles, the library displaying a plurality of different TCRs, the method comprising: i) obtaining a plurality of nucleic acids that encode different TRAV alpha chain variable domains; ii) obtaining a plurality of nucleic acids that encode different TRBV beta chain variable domains, wherein the plurality of nucleic acids that encode different TRBV gene products does not comprise nucleic acids that encode at least one of TRBV5-1, 5-3, 5-4, 5-5, 5-6, 5-7 or 5-8 beta chain variable domains; iii) cloning the TRAV alpha chain variable domain encoding nucleic acids into expression vectors; iv) cloning the TRBV beta chain variable domain encoding nucleic acids into the same or different vectors; and v) expressing the vectors in particles, thereby generating a library consisting essentially of TCRs comprising an alpha chain variable domain and a beta chain variable domain encoded by the nucleic acids.

The plurality of nucleic acids may not comprise nucleic acids that encode one or more of TRBV10-2, TRBV10-3, TRBV2, TBVB9, and/or TRBV14 gene product. The plurality of nucleic acids may include nucleic acids that encode a TRBV5-1 gene product. Alternatively, the plurality of nucleic acids may not comprise nucleic acids that encode any TRBV5 gene product.

The nucleic acids may be obtained entirely or partially by PCR using mRNA obtained from donor blood. Alternatively, the nucleic acids may be obtained entirely or partially by synthetic means, for example using solid phase DNA synthesis, such as carried out commercially by Life Technologies. The nucleic acids of i) and ii) may be obtained by copying/amplifying the nucleotide sequence trans cDNA, which has been made from mRNA from a donor's T cell repertoire. The nucleic acids that are obtained may encode different TRAV alpha or TRBV beta chain variable domains, excluding one or more of TRBV5-1, 5-2, 5-3, 5-4, 5-5, 5-6, 5-7 or 5-8. They may also exclude TRBV10-2, TRBV10-3, TRBV2, TBVB9, and/or TRBV14. Alternatively, nucleic acids encoding TRBV5-1 may be included. The library generated may be a library consisting essentially of TCRs comprising an alpha chain variable domain and a beta chain variable domain, wherein the beta chain variable domain does not comprise one or more of a TRBV5-1, 5-3, 5-4, 5-5, 5-6, 5-7 or 5-8 gene product. The beta chain variable domain may also not comprise a TRBV10-2, TRBV10-3, TRBV2, TBVB9, and/or TRBV14 gene product. The beta chain variable domain may not comprise any TRBV5 gene product. The beta chain variable domain may comprise a TRBV5-1 gene product.

The invention also provides a method of making a library of particles, the library displaying a plurality of different TCRs, the method comprising: i) obtaining a plurality of nucleic acids that encode different TRAV alpha chain variable domains using primers that hybridise to nucleic acids encoding TRAV alpha chain variable domains; ii) obtaining a plurality of nucleic acids that encode different TRBV beta chain variable domains using primers that hybridise to nucleic acids encoding TRBV beta chain variable domains, wherein primers that hybridise to one or more nucleic acid encoding a TRBV gene product do not comprise primers that hybridise to at least one nucleic acids encoding a TRBV5-1, 5-3, 5-4, 5-5, 5-6, 5-7 or 5-8 gene product; iii) cloning the TRAV alpha chain variable domain encoding nucleic acids into expression vectors; iv) cloning the TRBV beta chain variable domain encoding nucleic acids into the same or different vectors; and v) expressing the vectors in particles, thereby generating a library consisting essentially of TCRs comprising an alpha chain variable domain and a beta chain variable domain encoded by the nucleic acids to which said primers hybridise.

The method may not comprise primers that hybridise to at least one nucleic acid encoding one or more of a TRBV10-3, a TRBV10-2, a TRBV2, a TRBV9 and/or a TRBV14 gene product. The primers may include primers that hybridise to a nucleic acid encoding a TRBV5-1 gene product. The primers may not comprise primers that hybridise to a nucleic acid encoding any TRBV5 gene product.

Two single-stranded sequences will hybridize to each other even if there is not 100% sequence identity between the two sequences, depending on the conditions under which the hybridization reaction occurs and the composition and length of the hybridizing nucleic acid sequences.

Generally, the temperature of hybridization and the ionic strength (such as the $Mg^{2+}$ concentration) of the hybridization buffer will determine the stringency of hybridization. High stringency, such as high hybridization temperature and low salt in hybridization buffers, permits only hybridization between nucleic acid sequences that are highly similar, whereas low stringency, such as lower temperature and high salt, allows hybridization when the sequences are less similar. Calculations regarding hybridization conditions for attaining certain degrees of stringency can be readily carried out by the skilled person and are discussed in Sambrook et al., (1989) Molecular Cloning, second edition, Cold Spring Harbor Laboratory, Plainview, N.Y. (chapters 9 and 11). The skilled person will be able to optimise hybridization conditions according to the results from sensitivity and specificity tests.

The following is an exemplary set of hybridization conditions for use in the present invention:

Very High Stringency (detects sequences that share at least 90% identity)
 Hybridization: 5×SSC at 65° C. for 16 hours
 Wash twice: 2×SSC at room temperature (RT) for 15 minutes each
 Wash twice: 0.5×SSC at 65° C. for 20 minutes each High Stringency (detects sequences that share at least 80% identity)
 Hybridization: 5x-6×SSC at 65° C.–70° C. for 16-20 hours
 Wash twice: 2×SSC at RT for 5-20 minutes each
 Wash twice: 1×SSC at 55° C.–70° C. for 30 minutes each Low Stringency (detects sequences that share at least 50% identity)
 Hybridization: 6×SSC at RT to 55° C. for 16-20 hours
 Wash at least twice: 2x-3×SSC at RT to 55° C. for 20-30 minutes each.

The primers disclosed herein can hybridise to the nucleic acids encoding TRAV gene products or TRBV gene products under low stringency, high stringency, and very high stringency conditions.

The primer may bind with high stringency to the sequences encoding the alpha and beta chain variable domains. However, the primers may bind to some other loci which have high homology to the TRAV or TRBV to which they are designed to hybridise.

The nucleic acids of steps i) and ii) may be from a natural repertoire. Alternatively, these may be designed artificially. Non-natural mutations may be introduced to the alpha or beta variable domains, prior to step iii) or after step iii), i.e. the nucleic acid sequences may have non-natural mutations introduced prior to being cloned into vectors. Alternatively, the non-natural mutations may be introduced after the cloning steps of iii) and/or iv).

All or part of each of the nucleic acids encoding TRAV gene products or TRBV gene products may be obtained synthetically and/or designed artificially. In particular, the variable domain, the framework region, CDR1, CDR2 and/or CDR3 sequences may partially or fully obtained synthetically and/or designed artificially.

By "synthetically" it is meant sequences that have been chemically synthesised (i.e. other than by PCR or other biological techniques). All or part of the synthetic alpha or beta chain sequences may be chemically synthesised.

The amplification of the TRAV variable domains may be from a pre-prepared cDNA library, itself derived from donor mRNA, with a forward primer designed to specifically bind to the locus of interest. The reverse primer may be designed to specifically bind to (at least partially) the TCR alpha constant region, such that the resulting PCR product contains the TRAV nucleic acid sequence, some, all or none of the joining region and at least part of the constant region. Such primer design ensures that the variety and diversity of the alpha chain variable domain CDR3 region is captured, resulting in a large number of unique TCR alpha chain sequences being represented in the library of the invention. Alternatively, the CDR3 region may be amplified independently, for example using primers that specifically bind to framework sequences either side of CDR3. The resulting PCR products may be stitched to a TRAV sequence that does not have a CDR3.

Likewise, the amplification of the TRBV variable domain may be from an available cDNA library, with a forward primer designed to specifically bind to the locus of interest. The reverse primer may be designed to specifically bind to the TCR beta constant region, such that the resulting PCR product contains a TRBV nucleic acid sequence, some, all or none of the joining region (containing the D and J loci) and at least part of the constant region. Such primer design ensures that the variety and diversity of the beta chain variable domain CDR3 region is captured, resulting in a large number of unique TCR beta chain sequences being represented in the library of the invention. Alternatively, the CDR3 region may be amplified independently, for example using primers that specifically bind to framework sequences either side of CDR3. The resulting PCR products may be stitched to a TRBV sequence that does not have a CDR3.

The mRNA is obtained from at least one donor. By "from at least one donor" it is meant that the polypeptide sequence of all or part of the alpha or beta chain variable domain is substantially as it would naturally occur in a T cell of the donor from whom the mRNA is obtained. Preferably, the donor is human. The tissue type of the donor or donors may be known. The donor or donors may be HLA-A2 or A3 positive.

The resulting PCR products may be ligated into a phage vector directly if they contain the complete constant gene sequences, provided that the required ligation or recombination sequences are present in the vector and primer sequences. Alternatively, the alpha and beta PCR products may be stitched together with sequences containing the alpha constant domain gene sequence and the beta constant domain gene sequence respectively, in order to obtain complete TCR chain sequences. The alpha chain and beta chain may be randomly stitched together in order to increase the diversity in the phage library. The complete sequences may then be cloned into a phage vector, to be expressed as one open reading frame. An example of a suitable cloning strategy to produce a library of the invention is shown in FIG. 1.

Alternatively, other particle display formats may also be used to produce the libraries of the invention. Such methods are known to those of skill in the art and may include, but are not limited, to display on ribosome particles or yeast cells.

These display methods fall into two broad categories, in-vitro and in-vivo display.

All in-vivo display methods rely on a step in which the library, usually encoded in or with the genetic nucleic acid of a replicable particle such as a plasmid or phage replicon is transformed into cells to allow expression of the proteins or polypeptides. (Plückthun (2001) Adv Protein Chem 55 367-403). There are a number of replicon/host systems that have proved suitable for in-vivo display of protein or polypeptides. These include the following:
 Phage/bacterial cells
 plasmid/CHO cells
 Vectors based on the yeast 2 μm plasmid/yeast cells
 bacculovirus/insect cells
 plasmid/bacterial cells
 retroviral vector/mammalian cells In vivo display methods include cell-surface display methods in which a plasmid is introduced into the host cell encoding a fusion protein consisting of the protein or polypeptide of interest fused to a cell surface protein or polypeptide. The expression of this fusion protein leads to the protein or polypeptide of interest being displayed on the surface of the cell. The cells displaying these proteins or polypeptides of interest can then be subjected to a selection process such as FACS and the plasmids obtained from the selected cell or cells can be isolated and sequenced. Cell surface display systems have been devised for mammalian cells (Higuschi (1997) J Immunol. Methods 202 193-204), yeast cells (Shusta (1999) J Mol Biol 292 949-956) and bacterial cells (Sameulson (2002) J. Biotechnol 96 (2) 129-154). Display of single chain TCRs on the surface of yeast cells is known in the art (WO01/48145)

Numerous reviews of the various in-vivo display techniques have been published. For example, (Hudson (2002) Expert Opin Biol Ther (2001) 1 (5) 845-55) and (Schmitz (2000) 21 (Supp A) 5106-5112).

In-vitro display methods are based on the use of ribosomes to translate libraries of mRNA into a diverse array of protein or polypeptide variants. The linkage between the proteins or polypeptides formed and the mRNA encoding these molecules is maintained by one of two methods. Conventional ribosome display utilises mRNA sequences that encode a short (typically 40-100 amino acid) linker sequence and the protein or polypeptide to be displayed. The linker sequences allow the displayed protein or polypeptide sufficient space to re-fold without being sterically hindered by the ribosome. The mRNA sequence lacks a 'stop' codon, this ensures that the expressed protein or polypeptide and the RNA remain attached to the ribosome particle. The related mRNA display method is based on the preparation of mRNA sequences encoding the protein or polypeptide of interest and DNA linkers carrying a puromycin moiety. As soon as the ribosome reaches the mRNA/DNA junction translation is stalled and the puromycin forms a covalent linkage to the ribosome. For a review of these two related in-vitro display methods see (Amstutz (2001) Curr Opin Biotechnol 12 400-405).

Particularly preferred is the phage display technique which is based on the ability of bacteriophage particles to express a heterologous peptide or polypeptide fused to their surface proteins (Smith (1985) Science 217 1315-1317). The procedure is quite general, and well understood in the art for the display of polypeptide monomers. The display of dimeric proteins such as heterodimeric TCRs is also well established in the art (WO04/044004)

There are two main procedures which apply to both monomeric and dimeric display: Firstly (Method A) by inserting into a vector (phagemid) DNA encoding the heterologous peptide or polypeptide fused to the DNA encoding a bacteriophage coat protein (For example DNA encoding the proteins P3 or P8). The expression of phage particles displaying the heterologous peptide or polypeptide is then carried out by transfecting bacterial cells with the phagemid, and then infecting the transformed cells with a 'helper phage'. The helper phage acts as a source of the phage proteins not encoded by the phagemid required to produce a functional phage particle.

Secondly (Method B), by inserting DNA encoding the heterologous peptide or polypeptide into a complete phage genome fused to the DNA encoding a bacteriophage coat protein.

The expression of phage particles displaying the heterologous peptide or polypeptide is then carried out by infecting bacterial cells with the phage genome. This method has the advantage over the first method of being a 'single-step' process. However, the size of the heterologous DNA sequence that can be successfully packaged into the resulting phage particles is reduced. M13, T7 and Lambda are examples of suitable phages for this method.

A variation on (Method B) the involves adding a DNA sequence encoding a nucleotide binding domain to the DNA in the phage genome encoding the heterologous peptide be displayed, and further adding the corresponding nucleotide binding site to the phage genome. This causes the heterologous peptide to become directly attached to the phage genome. This peptide/genome complex is then packaged into a phage particle which displays the heterologous peptide. This method is fully described in WO 99/11785.

The phage particles can then be recovered and used to study the binding characteristics of the heterologous peptide or polypeptide. Once isolated, phagemid or phage DNA can be recovered from the peptide- or polypeptide-displaying phage particle, and this DNA can be replicated via PCR. The PCR product can be used to sequence the heterologous peptide or polypeptide displayed by a given phage particle.

The phage display of single-chain antibodies and fragments thereof, has become a routine means of studying the binding characteristics of these polypeptides. There are numerous books available that review phage display techniques and the biology of the bacteriophage. (See, for example, Phage Display—A Laboratory Manual, Barbas et al., (2001) Cold Spring Harbour Laboratory Press).

A third phage display method (Method C) relies on the fact that heterologous polypeptides having a cysteine residue at a desired location can be expressed in a soluble form by a phagemid or phage genome, and caused to associate with a modified phage surface protein also having a cysteine residue at a surface exposed position, via the formation of a disulphide linkage between the two cysteines. WO 01/05950 details the use of this alternative linkage method for the expression of single-chain antibody-derived peptides.

As mentioned above, αβ heterodimeric TCRs of the invention may have an introduced (non-native) disulphide bond between their constant domains. This can be achieved during the method of making the library of the invention by stitching the amplified nucleic acid sequence to a modified constant gene sequence. Such sequences may include those which have a TRAC constant domain sequence and a TRBC1 or TRBC2 constant domain sequence except that Thr 48 of TRAC and Ser 57 of TRBC1 or TRBC2, with reference to IMGT numbering, are replaced by cysteine residues, the said cysteines forming a disulphide bond between the TRAC constant domain sequence and the TRBC1 or TRBC2 constant domain sequence of the TCRs of the library.

With or without the introduced inter-chain bond mentioned in the preceding paragraph, αβ heterodimeric TCRs of the invention may have a TRAC constant domain sequence and a TRBC1 or TRBC2 constant domain sequence, and the TRAC constant domain sequence and the TRBC1 or TRBC2 constant domain sequence of the TCR may be linked by the native disulphide bond between Cys4 of exon 2 of TRAC and Cys2 of exon 2 of TRBC1 or TRBC2.

Alternatively, the TCR alpha chain variable domain and the TCR beta chain variable domain may be expressed as a single chain polypeptide. Such a configuration may include a non-native disulphide bond between mutated amino acid residues.

The invention also provides a method of obtaining a T cell receptor that specifically binds a peptide antigen, comprising screening the library according to the first aspect of the invention with the peptide antigen.

The screening may include one or more steps as set out below
- a) panning the library using as a target the peptide antigen
- b) repeating step a) one or more times
- c) screening the phage clones identified in step a) or b)
- d) identifying a TCR that specifically binds the peptide antigen.

In accordance with step (b), step (a) may be repeated once, twice, 3 times, 4 times, 5 times, or 6 times. It may be repeated up to 10 times. Step (a) may be repeated up to 20 times.

By panning it is meant that the phage clones are allowed to contact an antigen and the bound phage clones separated from the non-bound phage clones. This may include immobilising the antigen on a solid support such as tubes, magnetic beads, column matrices, or BiaCore sensorchips. Antigen attachment may be mediated by non-specific adsorption, or by using a specific attachment tag such as a biotinylated antigen and a streptavidin coated surface. An alternative method may include panning on intact cells. (Hoogenboom, H. R., et al (1998) Immunotechnology, 4(1), 1-20). The phage clones that do not bind (i.e. phage that do not display a TCR that binds to the antigen) are washed away. The bound phage clones may then be eluted by; enzymatic cleavage of a protease site, such as trypsin, between the TCR beta chain and gene III; extremes of pH; or competition with excess antigen. These phage clones may be taken through further rounds of panning, or on to screening experiments to identify clones with optimal binding characteristics.

The screening may be carried out, for example, by ELISA-based methods with either coated antigen or intact cells and may be in 96-well format; where whole cells are used, screening may be carried out using flow cytometry. Screening for binding affinity and kinetics may be carried out using surface plasmon resonance for example on a BiaCore instrument, or using a quartz crystal microbalance. Screening methods are described in Pande, J., et al. (2010). Biotechnol Adv 28(6): 849-58. As known to those skilled in the art further suitable methods for screening biomolecular interactions of this type are available including: the Octet system from ForteBIO, which utilizes BioLayer Interferometry (BLI) to measure biomolecular interactions in real time and provide information on affinity and kinetics; the Amplified Luminescent Proximity Homogenous Assay (e.g. AlphaScreen™) in which potentially interacting molecules are attached to 'donor' and 'acceptor' beads that have particular fluorescent properties when in close proximity; the Scintillation Proximity Assay in which interactions are assessed by transfer of beta particles between molecules in close proximity; other optical interfacial assays as described in, for example, WO 2004/044004.

Specificity may be determined by testing the identified TCRs for binding to other peptides other than the peptide antigen used to screen the library. If binding occurs to other peptides, the TCR may be considered to be non-specific. Specificity may be assessed using the methods identified above.

The peptide antigen may be a known antigen, such as those described in Bridgeman, J. S., et al. (2012) Immunology, 135(1), 9-18. The method of screening the library of the invention may also be used with novel peptide antigens, in order to identify specifically binding TCRs that may prove useful in therapeutic areas.

A final aspect of the invention provides an isolated cell displaying on its surface a TCR according to the invention, i.e. an isolated T cell receptor (TCR) comprising a TCR alpha chain variable domain comprising a TRAV gene product and a TCR beta chain variable domain comprising a TRBV gene product obtained from a library of the first aspect of the invention, wherein the TCR specifically binds a peptide antigen. The cell may be a T cell. The cell may be a human, murine or other animal cell.

There are a number of methods suitable for the transfection of T cells with DNA or RNA encoding the TCRs of the invention. (See for example Robbins et al., (2008) *J. Immunol.* 180: 6116-6131). T cells expressing the TCRs of the invention will be suitable for use in adoptive therapy-based treatment of diseases such as cancers, viral infections, autoimmune diseases, inflammatory diseases, parasitic infections and bacterial infections. As will be known to those skilled in the art there are a number of suitable methods by which adoptive therapy can be carried out. (See for example Rosenberg et al., (2008) *Nat Rev Cancer* 8 (4): 299-308).

For use in adoptive therapy, the invention also includes cells harbouring a TCR expression vector which comprises nucleic acid encoding the TCR of the invention in a single open reading frame or two distinct open reading frames. Also included in the scope of the invention are cells harbouring a first expression vector, which comprises nucleic acid encoding the alpha chain of a TCR of the invention, and a second expression vector, which comprises nucleic acid encoding the beta chain of a TCR of the invention. Alternatively, one vector may express both an alpha and a beta chain of a TCR of the invention.

The TCRs of the invention intended for use in adoptive therapy may be glycosylated when expressed by the transfected T cells. As is well known, the glycosylation pattern of transfected TCRs may be modified by mutations of the transfected gene (Kuball J et al. (2009), J Exp Med 206(2): 463-475).

For administration to patients, T cells transfected with TCRs of the invention may be provided in pharmaceutical composition together with a pharmaceutically acceptable carrier. Cells in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms. Suitable compositions and methods of administration are known to those skilled in the art, for example see, Johnson et al. *Blood* (114):535-46 (2009), with reference to clinical trial numbers NCI-07-C-0175 and NCI-07-C-0174.

The pharmaceutical composition may be adapted for administration by any appropriate route such as a parenteral (including subcutaneous, intramuscular, intravenous, or intraperitoneal), inhalation or oral route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated such as cancer, viral infection, autoimmune disease, inflammatory disease, bacterial infection or parasitic infection, the age and condition of the individual to be treated, etc. For example, a suitable dose range for an ImmTAC reagent (a soluble TCR fused to an anti-CD3 domain) may be between 25 ng/kg and 50 µg/kg. A physician will ultimately determine appropriate dosages to be used.

TCRs of the inventions may also be may be labelled with an imaging compound, for example a label that is suitable for diagnostic purposes. Such labelled high affinity TCRs are useful in a method for detecting a TCR ligand selected from CD1-antigen complexes, bacterial superantigens, and MHC-peptide/superantigen complexes which method comprises contacting the TCR ligand with a high affinity TCR (or a multimeric high affinity TCR complex) which is specific for the TCR ligand; and detecting binding to the TCR ligand. In tetrameric high affinity TCR complexes (formed, for example) using biotinylated heterodimers) fluorescent streptavidin (commercially available) can be used to provide a detectable label. A fluorescently-labelled tetramer is suitable for use in FACS analysis, for example to detect antigen presenting cells carrying the peptide antigen for which the high affinity TCR is specific.

A high affinity TCR (or multivalent complex thereof) of the present invention may alternatively or additionally be associated with (e.g. covalently or otherwise linked to) a therapeutic agent which may be, for example, a toxic moiety for use in cell killing, or an immunostimulating agent such as an interleukin or a cytokine. A multivalent high affinity TCR complex of the present invention may have enhanced binding capability for a TCR ligand compared to a non-multimeric wild-type or high affinity T cell receptor heterodimer. Thus, the multivalent high affinity TCR complexes according to the invention are particularly useful for tracking or targeting cells presenting particular antigens in vitro or in vivo, and are also useful as intermediates for the production of further multivalent high affinity TCR complexes having such uses. The high affinity TCR or multivalent high affinity TCR complex may therefore be provided in a pharmaceutically acceptable formulation for use in vivo.

High affinity TCRs of the invention may be used in the production of soluble bi-specific reagents. In a preferred embodiment, these are ImmTAC reagents. ImmTAC reagents comprise a soluble TCR, fused via a linker to an anti-CD3 specific antibody fragment.

Further details including how to produce such reagents are described in WO10/133828. Preferred or optional features of each aspect of the invention are as for each of the other aspects mutatis mutandis. Accordingly, although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Preparation of cDNA for Construction of TCR Phage Display Libraries
Isolation of mRNA from Peripheral Blood Lymphocytes (PBLs)
RNA was extracted from PBLs obtained from volunteer donors of known HLA type. RNA extraction was carried out using TRI reagent (Sigma, Cat. No. T9424), in accordance with the manufacturer's recommended protocol. mRNA was subsequently isolated using µMACS™ mRNA Isolation Kits (Miltenyi, Cat. No. 130-075-101), as directed by the manufacturer.

Preparation of cDNA from mRNA
cDNA was synthesised from the mRNA using SMART-Scribe™ Reverse Transcriptase (Clontech, 639536), in accordance with the manufacturer's recommended protocol. cDNA was further purified using S.N.A.P. Gel Purification Kit (Invitrogen, 45-0078).

Example 2

Phage Library Construction
An outline of library construction is shown in FIG. 1 and the corresponding primer sequences detailed in FIGS. 2, 3 and 4. TCR chains of the desired TRAV or TRBV type were amplified by PCR from purified cDNA using TRAV or TRBV specific forward primers, and reverse primers which anneal within either the TRAC (primer YOL237) or the TRBC regions (primer YOL 240). The primer sets were designed with reference to the known sequences of human TCR chains (T Cell Receptor Facts Book, Lefranc and Lefranc, Publ. Academic Press 2001). TRAV and TRBV specific primers may be PTO modified at the 3' end (PTO modification indicates inclusion of a phosphorothioate bond in the phosphate backbone of the oligonucleotide, wherein a sulphur atom substitutes for a non-bridging oxygen). The resulting PCR products comprised the full variable domain sequence and a truncated constant domain (labelled A and B in FIG. 1). To produce libraries containing more than one TRAV/TRBV, each chain type was amplified separately and the resulting PCR products pooled in equal amounts, such that fragments labelled A and/or B in FIG. 1 contained a mix pool of chain types. The remaining C-terminal section of the TRAC and TRBC2 domains, containing the non-native cysteine residues, were amplified by PCR from a separate cloning vector using the primers YOL236 and YOL238 for TRAC, and YOL239 and YOL22 for TRBC2 (labelled C and D in FIG. 1). Purified NC and B/D fragments were then stitched together in separate reactions via their overlapping primer regions (YOL237/YOL236 and YOL240/YOL239 respectively). The resulting A-C and B-D fragments were gel purified and stitched together via overlap PCR. This final stitching reaction results in random recombination between alpha chains and beta chains. The fragments were ligated into a suitable phagemid vector, termed pIM672 (pIM672 is based on the pEX922 vector previously described (see WO2005116074)), from which the alpha and beta chains were expressed as independent polypeptide chains, linked by a non-native disulphide bond. The vector was then used to transform highly transformation efficient electro-competent TG1 E. coli cells. Cultures were plated on 2xTYEag (EzMix, Sigma, Cat. No. Y2627 plus 100 µg/ml ampicillin and 2% glucose) agar plates overnight at 30° C., and the resultant cell lawns scraped into a small volume of 2xTYag medium containing 100 µg/ml ampicillin, 20% glycerol and 2% glucose. Glycerol stocks of the libraries were stored at −80° C.

Example 3

Library Propagation and Panning
Propagation of Phage Particles
An aliquot of phage library glycerol stock, sufficient to cover the diversity of the library, was used to inoculate 2xYTag media, to an initial OD600 of 0.05. The cultures were then incubated to an OD600 of about 0.5. Helper phage were then added at an infection ratio of ~20:1 phage to E. coli, The cultures were then mixed by inverting and incubated for 30 min at 37° C. The cultures were centrifuged and the pellets resuspended in 2xYTak (as 2xYTag but in the absence of glucose and with the addition of 50 µg/ml kanamycin) and subsequently incubated at 26° C. for 16 h with shaking.

Isolation of Phage Particles

The cultures were pooled, centrifuged and the supernatant collected and filtered at 0.45 µm. The eluate was mixed with 7 ml PEG/NaCl (20% PEG-8000 (Sigma Cat. No. 5413), 2.5M NaCl) and incubated on ice for 30 min. The sample was then pelleted and the supernatant discarded. The pellet was resuspended in 10 ml in PBS (Dulbeccos Sigma Cat. No. D8537—no Mg, no Ca) and re-centrifuged. The resulting supernatant was collected, mixed with 5 ml PEG/NaCl and stored on ice for 30 min. After centrifuging, the pellet was resuspended in 3 ml PBS, re-centrifuged, and the supernatant collected. An estimate of the phage concentration was determined using a Nanodrop spectrophotometer, where the number of phage per ml=OD260×(22.14×10$^{10}$).

Panning

Purified phage particles were mixed with 3% MPBS buffer (PBS (Dulbeccos Sigma Cat. No. D8537—no Mg, no Ca) plus 3% milk powder, previously incubated with streptavidin-coated paramagnetic beads, and then treated with 15 mM EDTA followed by extensive dialysis, and finally filtered at 0.22 µm) and incubated at room temperature for 1 h. 10% (v/v) Tween-20 was then added plus 100 nM or 1 µM biotinylated peptide-HLA. Samples were mixed at room temperature for 60 min. Phage-biotinylated-HLA complexes were rescued by the addition of streptavidin-coated paramagnetic beads pre-blocked in 3% MPBS buffer, and incubated at room temperature for 7 min. After capture, beads were isolated using a magnetic concentrator (Dynal) and washed three times with 3% MPBS (not EDTA treated) and twice with PBS-0.1% Tween. Phage particles were eluted in 0.5 ml TBSC (10 mM Tris, pH7.4, 137 mM NaCl, 1 mM CaCl$_2$ and 0.1 mg/ml trypsin) for 25 min at room temperature and 5 min at 37° C. with gentle rotation.

Eluted phage particles were used to infect early log phase TG1 E. coli cells. Cultures were incubated for 37° C. for 30 min and subsequently plated out onto YTEag (10 g Tryptone, 5 g yeast extract, 8 g NaCl, 15 g Bacto-Agar in 1 L MQ-water, plus 100 µg/ml ampicillin, and 2% glucose) in serial dilutions of 1 µl, 0.1 µl and 0.01 µl. The remaining culture was concentrated and also plated onto YTEag. Plates were incubated at 30° C. for 16 h. The following day, colonies from the plates were added to 2xTYag, frozen on dry ice and stored at −80° C. for the next round of panning. Colonies from each selection were analysed by PCR to check for full-length inserts.

After the third round of selection, colonies were scrapped from agar plates and used to inoculate sterile 2xTYag in a 96 well Cellstar cell culture plate at one clone per well. Plates were incubated at 26° C. for 16 h with shaking. These cultures were then used to inoculate fresh 2xTYag media in 96 well plates and incubated for 30 min at 37° C. with shaking until OD600=0.5. Helper phage were then added to each well at 20:1 phage—E. coli infection ratio and the plates incubated for 30 min at 37° C. without shaking. Pellets were collected by centrifugation and resuspended in 2xYTak. Plates were incubated for 16 h at 26° C. with shaking. Cells were then pelleted and supernatant collected for ELISA screening.

Example 4

Detection of phage particles bearing antigen-specific TCR by ELISA screening Phage clones that bound to a given peptide-HLA complex were identified by ELISA screening. ELISA plates were prepared using biotinylated peptide-HLA(s). Detection was carried out using an anti-Fd antibody (Sigma, Cat. No. B7786) followed by a monoclonal anti-rabbit IgG peroxidase conjugate (gamma chain specific clone RG96) (Sigma, Cat. No. A1949). Bound antibody was detected using the KPL labs TMB Microwell peroxidase Substrate System (Cat. No. 50-76-00). The appearance of a blue colour indicated the phage clone had bound to the peptide-HLA in that well.

For initial ELISA screening, phage clones were added to the plate in duplicate with the first well (labelled '+') containing the peptide-HLA complex that was used to pan the library and the second (labelled '−') containing an alternative peptide-HLA complex. No binding in the alternative peptide-HLA well indicated that binding was specific. Further ELISA specificity tests were performed using a panel of up to 10 alternative peptide-HLA complexes.

The DNA sequences of the TCRs from ELISA positive phage clones may be obtained by sequencing using methods known to those skilled in the art Example 5

Construction and Panning of a Library Comprising Multiple TRBVs but without TRBV5 and TRBV10.2/3 (I)

A library was prepared according to Examples 1 and 2, comprising a TRAV21 alpha chain and multiple TRBV chains. In this example the fragments amplified by TRBV primers 5-1, 5-4, 5-5/6/7, 10-2/3 and 11-3 were omitted during library construction, thereby producing a library with multiple TRBV chains but without TRBV5, TRBV10-2/3 and 11-3.

The library was panned according to Example 3 with six different peptide-HLA complexes, and detection carried out according to Example 4. FIG. 5a shows representative ELISA plates obtained after panning with two different peptide-HLA complexes. Of the six peptide-HLA complexes used to pan this library, initial ELISA screening identified specific phage clones for three of these. FIG. 5b shows the results of further ELISA specificity tests for two of the identified clones, against a panel of 10 alternative peptide-HLA complexes. In each case binding was only observed to the cognate peptide-HLA complex.

Comparative Data

A second library was prepared using the same method except that the fragments amplified by TRBV primers 5-1, 5-4, 5-5/6/7 and 10-2/3 were included during library construction, thereby producing a library with multiple TRBV chains including TRBV5 and TRBV10-2/3. For clarity, TRBV 11-3 was also excluded from this comparative library.

The library was panned according to Example 3 with the same six peptide-HLA complexes as used above, and detection carried out according to Example 4. In this case no antigen specific phage clones were identified in an initial ELISA screen.

FIG. 6a shows representative ELISA plates obtained after panning against two different peptide-HLA complexes. In all cases, where binding was observed in the first well, binding was also observed in the second, indicating that the TCRs displayed by these phage clones also recognised an alternative peptide-HLA complex and were therefore not specific. FIG. 6b shows representative ELISA specificity tests for two of the identified clones, against a panel of 8 alternative peptide-HLA complexes. The data confirm that the TCRs obtained from the library recognise other peptide-HLA complexes in addition to the cognate complex and were therefore not specific.

The data in this example demonstrate that a library comprising a single alpha chain and multiple beta chains but without TRBV5 and TRBV10.2/3 can be used to isolate useful TCRs (i.e. TCRs with a high degree of specificity for target peptide-HLA complex).

Example 6

Construction and Panning of a Library Comprising Multiple TRBVs but without TRBV5 and TRBV10.2/3 (II)

A library was prepared according to Examples 1 and 2, comprising a TRAV12-2 alpha chain and multiple TRBV chains. In this example the fragments amplified by TRBV primers 5-1, 5-4, 5-5/6/7, 10-2/3, and 11-3 were omitted during library construction, thereby producing a library with multiple TRBV chains but without TRBV5, TRBV10-2/3 and TRBV11-3.

The library was panned according to Example 3 with six different peptide-HLA complexes, and detection carried out according to Example 4. FIG. 7a shows representative ELISA plates obtained after panning with two different peptide-HLA complexes. Of the six peptide-HLA complexes used to pan this library, initial ELISA screening identified specific phage clones for four of these. FIG. 7b shows the results of further ELISA specificity tests for two of the identified clones, against a panel of 10 alternative peptide-HLA complexes. In each case binding is only observed to the cognate peptide-HLA complex.

Comparative Data

A second library was prepared using the same method as the first except that the fragments amplified by TRBV primers 5-1, 5-4, 5-5/6/7 and 10-2/3 were included during library construction, thereby producing a library with multiple TRBV chains including TRBV5 and TRBV10-2/3. For clarity, TRBV 11-3 was also excluded from this comparative library.

The library was panned according to Example 3 with the same six peptide-HLA complexes as used above, and detection carried out according to Example 4. In this case no antigen specific phage clones were identified from the initial ELISA screen.

This data in this example demonstrate that a library comprising a single alpha chain and multiple beta chains but without TRBV5 and TRBV10.2/3 can be used to isolate useful TCRs.

Example 7

Construction and Panning of a Library Comprising Multiple TRBVs but without TRBV5, TRBV10.2/3, TRBV2 and TRBV9

A further library was prepared as described in Example 5, comprising a TRAV21 alpha chain and multiple beta chains, except that the fragments amplified by TRBV primers TRBV2 and TRBV9 were also omitted during library construction in addition to TRBV primers 5-1, 5-4 and 5-5/6/7, 10-2/3 and 11-3, thereby producing a library with multiple TRBV gene products but without TRBV2, TRBV9, TRBV5, TRBV10-2/3, and TRBV 11-3 gene products.

The library was panned against the same six antigens used in Example 5. Subsequent ELISA screening indicated antigen specific TCRs could be isolated from the library. Including for one antigen for which no antigen specific TCRs were isolated using the library of Example 5.

FIG. 8a shows a representative ELISA plate obtained after panning with one peptide-HLA complex. FIG. 8b shows further specificity ELISA test for a TCR obtained from the library.

These data in this example demonstrate that a library comprising a single alpha chain and multiple beta chains but without TRBV5 TRBV10.2/3, TRBV2 and TRBV9 can be used to isolate useful TCRs.

Example 8

Construction and Panning of the Library Comprising a Single TRAV and 5 TRBVs

A library was constructed according to Examples 1 and 2, comprising a TRAV21 alpha chain and five beta chains. The beta chain fragments amplified by the following primers were included: TRBV3-1, 12-3/4, 7-9, 6-4 and 18.

The library was panned according to Example 3 with various peptide-HLA complexes and detection carried out according to Example 4. Antigen specific TCRs were obtained.

FIG. 9a shows representative ELISA plates obtained after panning. FIG. 9b shows further specificity ELISAs for TCRs obtained from the library.

The data in this example demonstrate that a library comprising a single alpha chain and five beta chains but without TRBV5-4, TRBV5-5/6/7 and TRBV10-2/3, TRBV2, TRBV9, and TRBV14 can be used to isolate useful TCRs.

Example 9

Construction and Panning of a Library Comprising 5 TRAVs and 5 TRBVs

A library was constructed according to Examples 1 and 2, comprising 5 TRAV chains and 5 TRBV chains. The alpha chain fragments amplified by the following primers were included: TRAV 12-1, 13-1, 17, 19 and 29. The beta chain fragments amplified by the following primers were included: TRBV 5-1, 12-3/4, 19, 20-1, 28.

The library was panned according to Example 3 with various peptide-HLA complexes and detection carried out according to Example 4. Antigen specific TCRs were obtained.

FIG. 10a shows representative ELISA plates obtained after panning. FIG. 10b shows further specificity ELISAs for TCRs obtained from the library.

The data in this example demonstrate that a library with 5 alpha chains and 5 beta chains but without TRBV5-4, TRBV5-5/6/7 and TRBV10-2/3, TRBV2, TRBV9, and TRBV14 can be used to isolate useful TCRs.

Example 10

Construction and Panning of a Library Comprising Multiple TRBVs but without TRBV5 and TRBV10.2/3, in Single Chain Format.

Further libraries were prepared according to Examples 1 and 2, except that the TCRs displayed by the phage particles were expressed in single chain format. Specifically, the alpha variable regions (fragment A, FIG. 1) were linked via a short linker sequence to the beta variable regions (fragment B), and beta constant region (fragment D), thereby producing a single chain TCR in the format Vα-L-VβCβ.

One library comprised a TRAV21 alpha chain and multiple TRBV chains (as in Example 5), the other a TRAV12-2 alpha chain and multiple beta chains (as in Example 6). In both cases the fragments amplified by beta chain primers for TRBV5-4, TRBV5-5/6/7 and TRBV10-2/3 were omitted during library construction resulting in a library that does not essentially comprise these gene products. In addition, the fragments amplified by the following beta chain primers were also omitted, TRBV2, TRBV7-3/4/6/7/8, TRBV9, TRBV11-3, TRBV12-5, TRBV14 and TRBV16 meaning that the resulting library does also not essentially comprise any of these gene products.

The two libraries were panned according to Example 3 and detection carried out according to Example 4. Based on the results of panning with seven different antigens, including 6 HLA-A*02 and one HLA-A*03 antigen, specific TCRs, as determined by specificity ELISA, were obtained from both of the libraries.

FIG. 11a shows representative ELISA plates obtained after panning the library with two different peptide-HLA complexes. FIG. 11b shows further specificity ELISAs for TCRs obtained from the library.

Comparative Data

An additional two libraries were prepared as described above using the same alpha and beta chains except that in this case primers for TRBV5-4, TRBV5-5/6/7 and TRBV10-2/3 were included during library construction, meaning that the resulting library does comprise these gene products. In addition primers for TRBV2, TRBV9, and TRBV14 were also included, meaning that the resulting libraries also contain these gene products. For clarity, primers for TRBV7-3/4/6/7/8, TRBV11-3, TRBV12-5, and TRBV16 were omitted from all four libraries in Example 10.

Panning these libraries with the same antigens lead to the isolation of cross reactive TCRs.

FIG. 12a shows representative ELISA plates obtained after panning the library with two different peptide-HLA complexes. FIG. 12b shows further specificity ELISAs for TCRs obtained from the library. These data indicate that cross reactive TCRs are obtained from the comparative libraries.

The data in this example demonstrate that libraries comprising a single alpha chain and multiple beta chains but without TRBV5-4, TRBV5-5/6/7 and TRBV10-2/3, TRBV2, TRBV9, and TRBV14, in single chain format can be used to isolate useful TCRs.

Example 11

Construction and Panning of a Library Comprising Multiple TRAVs and Multiple TRBVs A library was constructed according to Examples 1 and 2 and comprising multiple TRAV and multiple TRBV chains. In this example the fragments amplified by primers for TRBV5-4, TRBV5-5/6/7, TRBV10-2/3 were omitted during library construction and in addition the fragments amplified by the following TRBV primers were also omitted during library construction: TRBV2, TRBV7-3/4/6/7/8, TRBV9, TRBV11-3, TRBV12-5, TRBV14 and TRBV16. All TRAV primers were included.

The library was constructed using TCRs in single chain format as described in Example 10. The library was panned according to Example 3 and detection carried out according to Example 4. Antigen specific TCRs were obtained.

Figure 13:
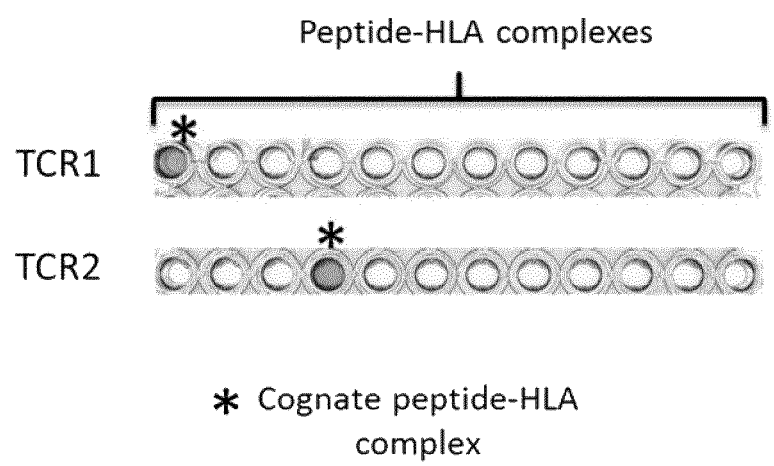
FIG. 13 shows further specificity testing of TCRs from positive ELISA clones from the library of Example 11.

FIG. 13 shows representative specificity ELISAs for TCRs obtained from the library.

The data in this example demonstrate that a library comprising multiple alpha and beta chains but without TRBV5-4, TRBV5-5/6/7 and TRBV10-2/3, TRBV2, TRBV9, and TRBV14 can be used to isolate useful TCRs.

Example 12

Biacore Analysis of TCRs Obtained from the Library
Method

The affinity for antigen of the TCRs isolated from libraries of the invention was determined by surface plasmon resonance using a BIAcore 3000 instrument and reported in terms of an equilibrium dissociation constant (KD). The TCRs sequences obtained from the phage clones were used to produce purified soluble versions of the TCRs using the method described in Boulter, et al., Protein Eng, 2003. 16: 707-711. Biotinylated specific and control peptide-MHC monomers were prepared as described in Garboczi, et al. Proc Natl Acad Sci USA 1992. 89: 3429-3433 and O'Callaghan, et al., Anal Biochem 1999. 266: 9-15, and immobilized on to a streptavidin-coupled CM-5 sensor chips. All measurements were performed at 25° C. in PBS buffer (Sigma) supplemented with 0.005% Tween (Sigma) at a constant flow rate. To measure affinity, serial dilutions of the soluble TCRs were flowed over the immobilized peptide-MHCs and the response values at equilibrium were determined for each concentration. Equilibrium dissociation constants (KD) were determined by plotting the specific equilibrium binding against protein concentration followed by a least squares fit to the Langmuir binding equation, assuming a 1:1 interaction.

Figure 14:
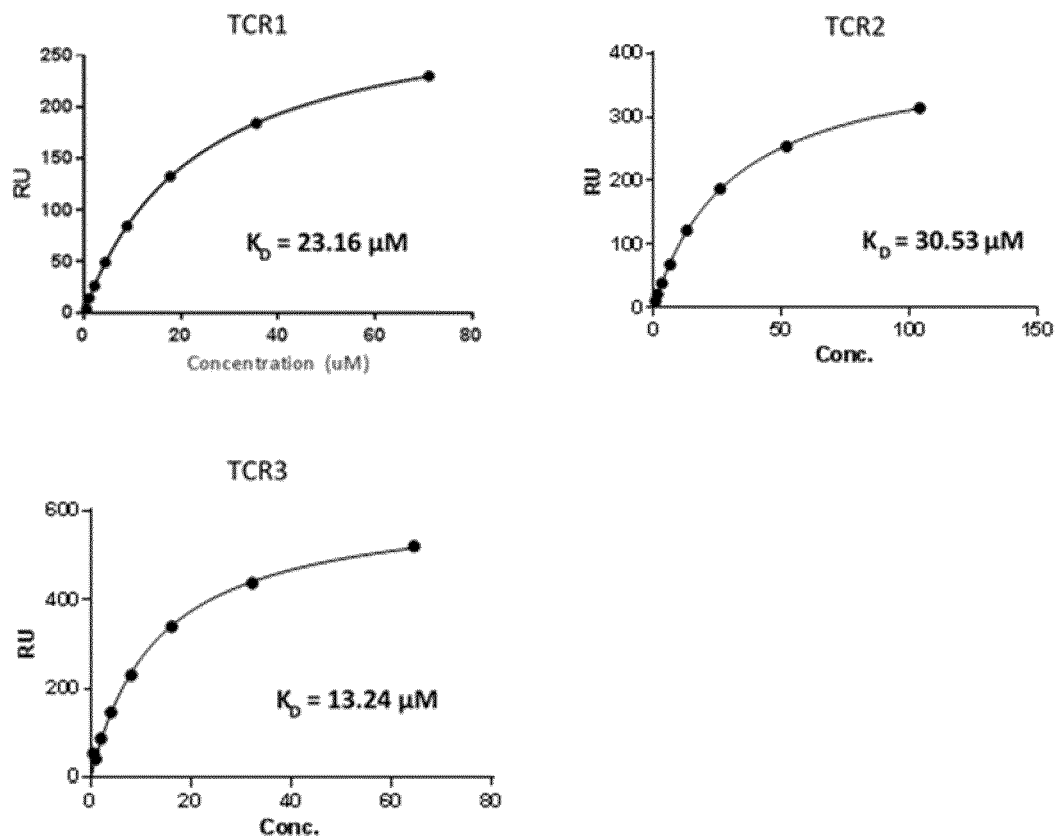
FIG. 14 shows Biacore binding data for three TCRs obtained from the libraries of the examples.

FIG. 14 shows Biacore equilibrium binding data for three TCRs obtained from the libraries of the examples. These data demonstrate that TCRs obtained from the libraries of the invention can bind cognate antigen with an affinity in the low micromolar (μM) range.

The invention claimed is:

1. A library of particles displaying a plurality of T cell receptors (TCRs), wherein the plurality of TCRs:
   i) consists essentially of TCRs comprising
      (a) an alpha chain, the alpha chain comprising an alpha chain variable domain from a natural repertoire of TCRs that have undergone thymic selection in a human donor, and
      (b) a beta chain, the beta chain comprising a beta chain variable domain from a natural repertoire of TCRs that have undergone thymic selection in a human donor and that does not comprise one or more of a TRBV5-1, 5-3, 5-4, 5-5, 5-6, 5-7 or 5-8 gene product; and
   ii) comprises more than one TRAV gene product and/or more than one TRBV gene product,
   wherein the TCRs are covalently attached to the particle, and
   wherein the particles are phage particles, ribosomes, yeast cells, or mammalian cells.

2. The library of claim 1, wherein the beta chain variable domain does not comprise either of a TRBV10-2 gene product and/or a TRBV10-3 gene product.

3. The library of claim 1, wherein the beta chain variable domain does not comprise a TRBV2 gene product, a TRBV9 gene product, and/or a TRBV14 gene product.

4. The library of claim 1, wherein the beta chain variable domain does not comprise a TRBV5 gene product.

5. The library of claim 1, wherein the beta chain variable domain comprises a TRBV5-1 gene product.

6. The library of claim 1, wherein the framework region, constant region, and CDR1, CDR2 and/or CDR3 sequence of the alpha and/or beta variable domain comprises at least one non-natural mutation.

7. The library of claim 1, wherein the alpha chain variable domain and the beta chain variable domain are displayed as a single polypeptide chain.

8. The library of claim 1, wherein the TCRs comprise a non-native disulfide bond between a constant region of the alpha chain and a constant region of the beta chain.

9. The library of claim 1, wherein the TCRs comprise a native disulfide bond between a constant region of the alpha chain and a constant region of the beta chain.

10. The library of claim 1, wherein each alpha chain and each beta chain comprises a dimerization domain.

11. The library according to claim 10, wherein the dimerization domain is heterologous.

12. The library of claim 1, wherein the particles are phage particles.

13. The library of claim 1, wherein the particles are ribosomes.

14. The library of claim 1, wherein the particles are yeast cells.

15. The library of claim 1, wherein the particles are mammalian cells.

16. A method of obtaining a T cell receptor (TCR) that specifically binds a peptide antigen, comprising screening the library of phage particles of claim 12 with the peptide antigen, the method comprising:
   a) panning the library using as a target the peptide antigen;
   b) repeating step a) one or more times;
   c) screening the phage particles identified in step a) or b); and
   d) identifying a TCR that specifically binds the peptide antigen.

17. A method of making the library of particles of claim 1, the library displaying a plurality of different TCRs, the method comprising:
   i) obtaining a plurality of nucleic acids from a natural repertoire that encode different TRAV alpha chain variable domains;
   ii) obtaining a plurality of nucleic acids from a natural repertoire that encode different TRBV beta chain variable domains, excluding nucleic acids that encode one or more of TRBV5-1, 5-3, 5-4, 5-5, 5-6, 5-7 or 5-8 beta chain variable domains;
   iii) cloning the TRAV alpha chain variable domain encoding nucleic acids into expression vectors;
   iv) cloning the TRBV beta chain variable domain encoding nucleic acids into the same or different vectors; and
   v) expressing the vectors in particles, thereby generating a library consisting essentially of TCRs comprising an alpha chain variable domain and a beta chain variable domain encoded by the nucleic acids.

18. A method of making the library of particles of claim 1, the library displaying a plurality of different TCRs, the method comprising:
   i) obtaining a plurality of nucleic acids from a natural repertoire that encode different TRAV alpha chain variable domains using primers that hybridize to nucleic acids encoding TRAV alpha chain variable domains;
   ii) obtaining a plurality of nucleic acids from a natural repertoire that encode different TRBV beta chain variable domains using primers that hybridize to nucleic acids encoding TRBV beta chain variable domains, excluding primers that hybridize to one or more nucleic acids encoding a TRBV5-1, 5-3, 5-4, 5-5, 5-6, 5-7 or 5-8 beta chain variable domains;
   iii) cloning the TRAV alpha chain variable domain encoding nucleic acids into expression vectors;
   iv) cloning the TRBV beta chain variable domain encoding nucleic acids into the same or different vectors; and
   v) expressing the vectors in particles, thereby generating a library consisting essentially of TCRs comprising an alpha chain variable domain and a beta chain variable domain encoded by the nucleic acids to which said primers hybridize.

19. The library of claim 1, wherein at least a plurality of the particles display a TRBV3-1 gene product.

* * * * *